United States Patent [19]
Wakefield et al.

[11] Patent Number: 5,919,761
[45] Date of Patent: Jul. 6, 1999

[54] PEPTIDES FOR HEPARIN AND LOW MOLECULAR WEIGHT HEPARIN ANTICOAGULATION REVERSAL

[75] Inventors: Thomas W. Wakefield; James C. Stanley; Philip C. Andrews, all of Ann Arobr, Mich.

[73] Assignee: The Board of Regents of the University of Michigan, Ann Arbor, Mich.

[21] Appl. No.: 08/436,703

[22] Filed: May 8, 1995

Related U.S. Application Data

[63] Continuation-in-part of application No. PCT/US94/12981, Nov. 10, 1994, which is a continuation-in-part of application No. 08/303,025, Sep. 8, 1994, Pat. No. 5,614,494, which is a continuation-in-part of application No. 08/152,488, Nov. 12, 1993, Pat. No. 5,534,619, which is a continuation-in-part of application No. PCT/US92/06829, Aug. 14, 1992.

[51] Int. Cl.⁶ .......................... A61K 38/03; A61K 38/10; A61K 38/16; C07K 14/00
[52] U.S. Cl. .............................. 514/12; 514/13; 530/324; 530/325; 530/326; 530/358
[58] Field of Search .................. 530/324, 325, 530/326, 358; 514/12, 13, 834

[56] References Cited

U.S. PATENT DOCUMENTS

| | | | |
|---|---|---|---|
| 4,792,525 | 12/1988 | Ruoslahti et al. | 435/240.243 |
| 5,272,261 | 12/1993 | Cardin et al. | 536/21 |
| 5,358,934 | 10/1994 | Borovsky et al. | 514/17 |
| 5,534,619 | 7/1996 | Wakefield | 530/324 |
| 5,614,494 | 3/1997 | Wakefield et al. | 514/12 |
| 5,721,212 | 2/1998 | Wakefield et al. | 514/12 |

FOREIGN PATENT DOCUMENTS

| | | |
|---|---|---|
| 47197 | 3/1982 | European Pat. Off. . |
| 9012866 | 11/1990 | WIPO . |
| 9404176 | 3/1994 | WIPO . |
| 95/13083 | 5/1995 | WIPO . |

OTHER PUBLICATIONS

Eur. J. Biochem, vol. 158, Issued 1986, McKay et al., "Rainbow Trout Protamines", pp. 361–366.

Journal of Vascular Surgery, vol. 18, No. 1, Issued 1993, DeLucia et al., "Efficacy and Toxicity of Differently Charged Polycatonic Protamine-like Peptides," pp. 49–60.

*Primary Examiner*—Jeffrey E. Russel
*Attorney, Agent, or Firm*—Benita J. Rohm; Raphael A. Monsanto

[57] ABSTRACT

Less toxic agents for reversal of heparin or low molecular weight heparin anticoagulation which are synthetic protamine-like polycationic peptides having a total cationic charge which is less than that of n-protamine. In preferred embodiments, arginine residues of n-protamine are replaced with lysine residues for ease of manufacture. Selective positively charged arginine residues have been replaced with an uncharged amino acid residue or its analog, such as glycine or glutamine, in order to reduce the total cationic charge on the polycationic peptide to the range of about [+14] to [+18], preferably [+16] to [+18]. In specific embodiments, there are sequences of 29 and 32 amino acid residues wherein 4 to 5 clusters of 2 to 4 positively charged amino acids are separated by 2 to 6 neutral amino acids. The C-terminus and the N-terminus can be modified to mitigate against in vivo degradation by carboxypeptidases and aminopeptidases. Another modification, specifically use of α-helix forming amino acids, such as glutamic acid, further promotes anticoagulation reversal. A still further modification includes the incorporation of a cell adhesion ligand, such as the RGD sequence, into the synthetic protamine-like polycationic peptide.

81 Claims, 8 Drawing Sheets

PEPTIDES FOR HEPARIN AND LOW MOLECULAR WEIGHT HEPARIN ANTICOAGULATION REVERSAL

This application is a continuation-in-part patent application of International Application No. PCT/US94/12981 filed on Nov. 10, 1994 which is a continuation-in-part patent application of U.S. Ser. No. 08/303,025 filed on Sep. 8, 1994, now U.S. Pat. No. 5,614,494, which is a continuation-in-part patent application of U.S. Ser. No. 08/152,488 filed on Nov. 12, 1993, now U.S. Pat. No. 5,534,619 issued on Jul. 9, 1996, which is a continuation-in-part patent application of International application Ser. No. PCT/US92/06829 filed on Aug. 14, 1992.

BACKGROUND OF THE INVENTION

1. Technical Field

This invention relates generally to agents for reversal of heparin and low molecular weight heparin anticoagulation, and more particularly, to novel peptide compositions which are less toxic variants of protamine.

2. Background of the Prior Art

Heparin, a highly sulfated polyanionic macromolecule comprising a group of polydiverse (molecular weight ranges from 5,000 to 30,000 daltons) straight-chain anionic mucopolysaccharides called glycosaminoglycans, is the most commonly used clinical anticoagulant. Its major clinical applications include, inter alia: treatment of thromboembolism; prophylactic treatment of patients at high risk for embolism; post-operative prevention of thromboembolism; and prevention of clotting and thrombus formation resulting from interventions in the circulatory system, such as cardiovascular diagnostic procedures, catheterization, surgery of the heart and vessels, and many other procedures including extracorporeal blood circulation, such as hemodialysis, use of artificial organs and organ transplantation. At the conclusion of these procedures, the anticoagulation effects of heparin must be neutralized or reversed in order to prevent the patient from bleeding.

Currently, protamine sulfate is the only available compound used to reverse heparin coagulation. Protamine sulfate is a polycationic peptide derived from salmon sperm, sometimes designated salmine protamine or n-protamine. Unfortunately, the use of protamine frequently results in adverse hemodynamic and hematologic side effects such as hypotension, bradycardia, pulmonary artery hypotension, depressed oxygen consumption, thrombocytopenia with pulmonary platelet sequestration, and leukopenia. In clinical use, significant systemic arterial hypertension and pulmonary artery hypertension occur in about 4% of the cases. In some instances, death has resulted. Considering cardiovascular procedures only, more than 450,000 patients per year in the United States can be expected to exhibit protamine-related side effects. Furthermore, many patients suffer adverse immunologic reactions to protamine. There is clearly a need for a safer, less toxic agent for reversal of heparin.

The major constituent of protamine is arginine, a highly alkaline cationic substance. Conventional salmine protamine is a mixture of highly cationic peptides. The most prevalent peptide is a 32 amino acid sequence having a total cationic charge of [+21]: ProArg$_4$Ser$_3$ArgProValArg$_5$ProArgValSerArg$_6$Gly$_2$Arg$_4$ (Sequence Listing ID No. 14). Positively charged arginine accounts for 67% of the total sequence and for all of the peptide's positive charge. In this sequence, there are four positively charged arginyl clusters connected by aminoacyl residues.

The efficacy of protamine for heparin neutralization may be, at least in part, a function of its positive charge. There is great potential for ionic interaction between the polycation protamine and the polyanion heparin. The therapeutic effect of standard heparin lies primarily in its ability to enhance inactivation of thrombin (T) by anti-thrombin III (AT-III). Further, heparin potentiates the ability of AT-III to inactivate both factor Xa and factor IIa (thrombin). Two dimensional crossed immunoelectrophoresis studies suggest that protamine dissociates AT-III:heparin complexes by virtue of its positive charge resulting in heparin anticoagulation reversal. When the complex is dissociated, AT-III returns to its unpotentiated state.

Other highly charged polycations, such as poly-I-lysine or polybrene, are capable of neutralizing heparin. However, both poly-I-lysine and polybrene have proven to be too toxic for clinical use. Therefore, the same positive charge which reverses the effect of heparin may be a cause of protamine's toxicity. In vitro data suggest that charge-related events may be toxic due to elaboration of specific vasodilatory factors, disruption of specific cellular organelles such as mitochondria, or by alteration in the pH of the intracellular or intraorganelle matrix.

In addition to unfractionated standard heparin, low-molecular weight heparin, or fractionated heparin, is beginning to find application in the practice of medicine. LMWH has now been recommended for cardiovascular surgery, and may be preferable to standard, unfractionated heparin for bolus injection during aortofemoral bypass surgery and cardiopulmonary bypass procedures. One example of a low molecular weight heparin currently being marketed is Logiparin (LHN-1, Novo, Denmark). Logiparin is produced from porcine intestinal mucosal heparin by enzymatic depolymerization using heparinase. Its molecular mass ranges from 600 to 20,000 daltons, with more than 70% of its molecular mass ranging between 1,500 and 10,000 daltons. Another low-molecular weight heparin is Enoxaparin (available from Rhone-Poulac, France). Enoxaparin is available for clinical use in the United States for venous thrombosis prophylaxis.

In general, low molecular weight heparins have an improved pharmacokinetic profile as compared to standard, unfractionated heparin, less antiplatelet activity (and, consequently, less bleeding potential), less lipolytic effect, and a half-life which is not dependent on the initial dose administered. Unfortunately, the use of protamine to reverse the anticoagulation effects of LMWH may result in the same undesired side effects produced by its use in connection with standard, unfractionated heparin. Moreover, protamine is known to incompletely reverse the anti-Xa activity of LMWH. There is, therefore, a need in the art for an improved agent for reversing the anticoagulation effects of LMWH.

It is, therefore, an object of this invention to provide improved agents for reversal of heparin or low molecular weight heparin anticoagulation.

It is also an object of this invention to provide improved agents for reversal of heparin or low molecular weight heparin anticoagulation which are relatively easy and inexpensive to synthesize.

It is a still further object of this invention to provide nontoxic, or less toxic, variants of protamine which will adequately reverse the effects of heparin or low molecular weight heparin anticoagulation.

SUMMARY OF THE INVENTION

The foregoing and other objects are achieved by this invention which provides synthetic protamine-like peptides which are useful as heparin or low molecular weight heparin anticoagulation reversal agents. The peptide compositions of the present invention may comprise a sequence of 20–40 amino acids having a total cationic charge of less than the [+21] charge of n-protamine, as determined by the number of positively charged amino acids in the sequence, and the ability to at least partially reverse the effects of heparin or low molecular weight heparin anticoagulation. Preferably, the total cationic charge on the peptide composition is in the range of [+14] to [+18].

In certain preferred embodiments, the distribution of positive residues in the peptide/protein remain similar to naturally-occurring protamine. Charge density, charge distribution and peptide length have been altered as will be described hereinbelow. However, a random or an even distribution of positive charges throughout the length is feasible provided that the total charge on the peptide is within the preferred range.

Invariably, arginine is the basic residue of the charged clusters in n-protamine. In some of the present embodiments, arginine residues have been replaced with lysine residues. Lysine, like arginine, carries a positive charge at physiological pH and is preferably used in the amino acid sequence due to technical difficulties which are encountered in the automated synthesis of multiple arginine-containing peptides. Further, the use of lysine simplifies interpretation of steric effects.

Of course, any positively charged amino acid, such as histidine, arginine or analogs thereof, such as ornithine or methyl arginine, can be used for inserting positive charges into the synthetic protamine-like peptide analogs in accordance with the present invention.

In preferred embodiments, the positively charged amino acids or lysines are arranged into groups of either two or four consecutive residues to simulate the grouped arrangement of arginine residues within the major component of n-protamine. In the embodiments described herein, peptide length has been kept constant at 29 amino acids. However, length can be varied, illustratively from about 20 to 40.

The aminoacyl connecting residues of n-protamine were replaced with glycine residues in order to simplify the structure and to simplify the synthesis and give flexibility to the molecule. Glycine has no side chains to sterically interfere with the charge-charge interaction between the protamine variant compounds and negatively charged heparin.

In advantageous embodiments, lysine residues were selectively replaced with the uncharged amino acid glutamine in order to decrease the number of positive charges on the molecule and to decrease the charge density. Glutamine has a similar hydrophilicity and size/steric configuration to lysine.

In addition to glutamine, any uncharged amino acid, such as alanine, serine, threonine, asparagine, proline, valine, isoleucine, leucine, or analogs thereof, may be used in the preparation of the synthetic peptide analogs of the present invention.

Proline occurs at the terminus of naturally-occurring protamine and has been retained in the embodiments presented herein in order to inhibit the breakdown of the peptide by circulating aminopeptidases. However, it is contemplated that the N- and C-terminus groups can be modified. An amide bond, for example, at the C-terminus might affect resistance to degradation while acetylation at the N-terminus might have a similar effect. These modifications of the N- and C-termini may also affect biological activity and/or toxicity.

We have discovered that the charge on the peptide molecule is directly proportional to the toxicity and the efficacy as an agent for the reversal of the anticoagulation effects of heparin. Therefore, we have developed synthetic protamine-like peptides with lower total cationic charge in order to reduce toxicity effects, but which retain enough positive charge for, at least partial, in vivo reversal of heparin. We have found that a total cationic charge of [+14] to [+21] on the molecule is advantageous for heparin reversal. In fact, the total cationic charge (as determined from the number of lysine residues) is a more important factor in heparin anticoagulation reversal than the specific amino acid composition. However, as the total cationic charge on the peptide increases, so does toxicity as measured by adverse hemodynamic effects. In a preferred embodiment of the invention, protamine variants having a charge in the range of [+14] to [+18], and preferably [+16] to [+18] have an improved efficacy to toxicity ratio for the reversal of heparin anticoagulation.

In preferred embodiments for the reversal of the anticoagulation effects of low molecular weight heparin, protamine variants having a charge in the range of [+16] to [+18] which have been amidated at the C-terminus and acetylated at the N-terminus to prevent in vivo degradation produce particularly efficacious results. In further advantageous embodiments, the number of amino acid residues in the peptide chain should be appropriate to facilitate alpha-helix formation on binding to the low molecular weight heparin, illustratively 28 or 32 in the case of amidated and acetylated compounds having charges of [+16] and [+18], respectively. Using alanine residues in the connecting amino acids between charged clusters increases stability of alpha-helix formation on binding low molecular weight heparin. Specific illustrative embodiments of this preferred embodiment include acetyl-PAK$_2$(AK$_2$A$_2$K$_2$)$_3$AK $_2$-amide [+16B] (Sequence Listing ID No. 1) and acetyl-PA(K$_2$A$_2$K$_2$A)$_4$K$_2$-amide [+18B] (Sequence Listing ID No. 2).

In other preferred embodiments of the invention, non α-helix forming amino acids, such as proline, are replaced by α-helix forming amino acids, such as glutamic acid. In specific preferred embodiments, acetyl-E(AK$_2$A$_2$K$_2$)$_4$-amide [+16BE] (Sequence Listing ID No. 3) and acetyl-EA$_2$(K$_2$A$_2$K$_2$A)$_4$K$_2$-amide [+18BE] Sequence Listing ID No. 4), has been found to reverse the anticoagulation effects of both low molecular weight heparin and standard heparin.

In still further preferred embodiments of the invention, cell adhesion ligands of the type which are known to bind to cell matrices, such as the fibronectin-receptor ligand "RGD" or the laminin-receptor ligand "YIGSR (Sequence Listing ID No. 18)," are included in the backbone structure of the protamine analogs. It is believed that inclusion of an RGD sequence, for example, in the sequence allows the protamine analog to bind to receptors on cell surfaces while still being exposed to the serum for interaction with heparin and/or LMWH. Binding to the receptor reduces the amount of free peptide in the bloodstream, thereby reducing the toxicity. A specific preferred embodiment of this aspect of the invention has the molecular formula Acetyl-EA(R$_2$A$_2$R$_2$A)$_4$R$_2$GRGDSPA-amide (Sequence Listing ID No. 5).

L-amino acids have been used in the preparation of the inventive compositions; however, D-amino acids or beta and delta forms may be used, and in fact, these other forms may reduce the levels of degradation in vivo.

Of course, compositions including a combination of one or more protamine-like peptide analogs of the present invention in combination with a suitable delivery vehicle, such as a parenteral vehicle of the type well-known in the art, are within the contemplation of the invention.

In a method aspect of the invention, an anticoagulation-reversing effective amount of a protamine-like peptide analog of the present invention, or a combination of such analogs, is administered to a living being in a suitable parenteral vehicle, for example. Dosage ranges are with the skill of a person of ordinary expertise in the art, illustratively 1:1 peptide:heparin (1 mg/100 IU heparin). As used herein, the term "anticoagulation-reversing effective amount" refers to the amount necessary to produce cessation of clinical bleeding and to cause return of quantitative coagulation tests to their baseline level.

The protamine-like peptide analogs of the present invention are synthesized from L-amino acids. However, the product is a partially racemic mixture which must be resolved and characterized. FDA regulations do not permit more than 50% D-amino acids for human usage. Of course, the peptide analogs should be sterilized prior to administration to humans or animals.

BRIEF DESCRIPTION OF THE DRAWING

Comprehension of the invention is facilitated by reading the following detailed description, in conjunction with the annexed drawings, in which:

FIG. 1a shows activated clotting time (ACT), FIG. 1b shows thrombin clotting time (TCT), FIG. 1c shows Heparin Antifactor Xa Activity, and FIG. 1d shows Heparin Antifactor IIa Activity;

FIG. 4a shows activated clotting time (ACT), FIG. 4b shows thrombin clotting time (TCT), FIG. 4c shows Heparin Antifactor Xa Activity, and FIG. 4d shows Heparin Antifactor IIa Activity; FIG. 5a shows activated clotting time (ACT), FIG. 5b shows thrombin clotting time (TCT), FIG. 5c shows Heparin Antifactor Xa Activity, and FIG. 5d shows Heparin Antifactor IIa Activity.

DETAILED DESCRIPTION OF THE INVENTION

Figure 1A:
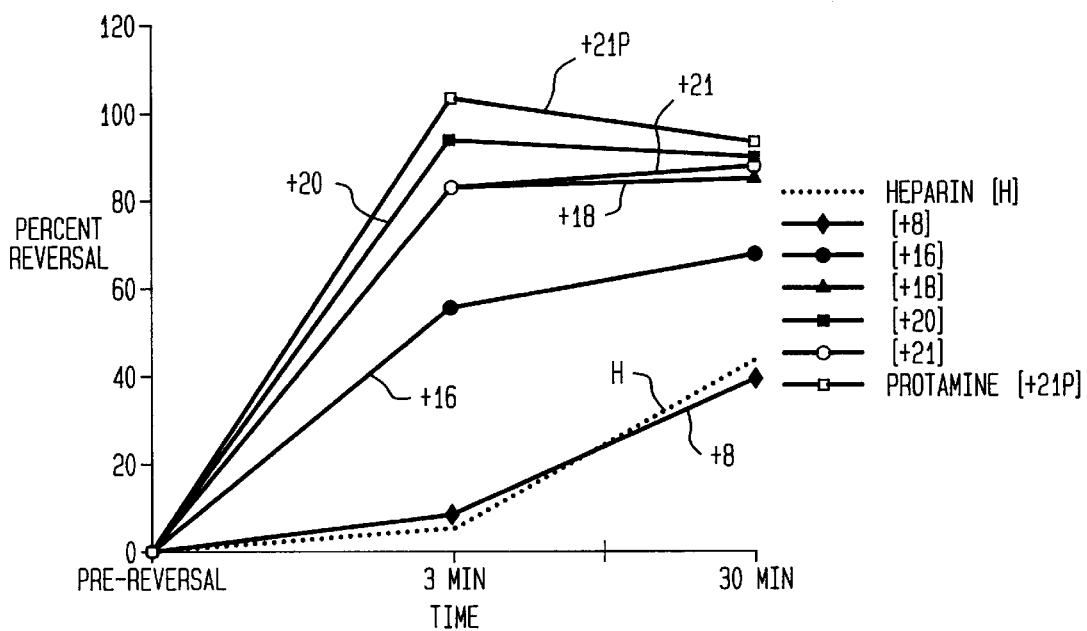
FIG. 1a through FIG. 1d are graphical representations of heparin anticoagulation activities achieved by n-protamine (Protamine [+21]) and selected synthetic protamine-like peptide analogs of the present invention plotted as a percent of reversal against time in minutes, more specifically.

The following definitions are used herein to denote the amino acids comprising the exemplary peptides of the present invention:

P=Pro proline
K=Lys=lysine
G=Gly=glycine
Q=Gln=glutamine
E=Glu=glutamic acid
R=Arg=arginine
S=Ser=serine
V=Val=valine
A=Ala=alanine
Y=Tyr=Tyrosine
D=Asp=Aspartate
I=Ile=Isoleucine
L=Leu=Leucine Synthesis of Protamine-Like Peptide Analogs Peptides of the present invention can be made by recombinant genetic technology, chemical methods, or protein synthesis techniques, such as automated fluorenyl-methoxycarbonyl (FMOC) and t-butyloxycarbonyl (TBOC) procedures. The resultant products may be purified and characterized by amino acid analysis and mass spectroscopy.

In illustrative embodiments, protamine-like peptide analogs were synthesized with an automated peptide synthesizer using FMOC-amino acids (Applied Biosystems, Model 431). Once synthesized, these peptides were purified on a polysulfoethyl polyaspartamide high pressure liquid chromatography (HPLC) cation exchange column diluted by a sodium sulfate salt gradient (0–0.2 M, pH 3.0), and desalted on a 300 Å pore diameter size exclusion HPLC (1 centimeter by 25 centimeters) using 15% acetonitrile, 50 mM formic acid buffer. Each purified peptide was characterized by amino acid analysis and mass spectroscopy to confirm purity prior to use. Inclusion of norleucine as an internal standard for amino acid analysis allowed accurate assessment of peptide concentration.

The following peptide analogs were synthesized so that the total number of lysine residues determined the total peptide cationic charge as set forth in Table 1. It is to be understood that the peptides listed in Table 1 are merely exemplary of the many different permutations and combinations of amino acids within the contemplation of the principles of the invention.

TABLE 1

| | Amino Acid Sequence | Total Cationic Charge |
|---|---|---|
| (1) | $P(K_2O_2G_4)_3K_2O_2$ | [+8]* |
| (2) | $P(KG)_{13}K$ | [+14] |
| (3) | $YP(KA)_{13}K$ | [+14] |
| (4) | $P(K_4G_4)_3K_4$ | [+16]* |
| (5) | $PK_4G_4(K_4G_2)_3K_2$ | [+18]* |
| (6) | $P(K_2G)_9K_2$ | [+20] |
| (7) | $P(K_4G_2)_4K_4$ | [+20]* |
| (8) | $PK_4S_3KPVK_6PKVSK_6G_2K_4$ | [+21]* |
| (9) | $PR_4S_3RPVR_5PRVSR_6G_2R_4$ (n-protamine) | [+21]* |

The peptide, designated (8) in Table 1, having a [+21] charge and the same sequence as n-protamine, was synthesized in order to compare the effect of the sole substitution of lysine for arginine. The peptides designated as (2) and (6) on Table 1 are examples of peptides in which the positive charges are not clustered. Preliminary studies indicate that these peptides exhibit similar efficacy and toxicity effects to the grouped compounds; provided that the total charge on the peptide is maintained in the appropriate range.

I. Studies on the Reversal of the Anticoagulation Effects of Standard Heparin

The ability of the protamine-like peptides of the present invention to reverse the anticoagulation effects of standard, unfractionated heparin was assessed by in vivo canine studies conducted with the peptides marked on Table 1 with an asterisk.

in vivo Canine Studies

Five female dogs (8–15 kg) received standard, unfractionated heparin (150 IU/kg IV) followed by reversal with either control commercial salmine protamine (n-protamine, [+21]) or one of the five variants listed hereinabove in Table 1 and marked with an asterisk (1.5 mg/kg IV over 10 seconds). As used hereinafter, the peptides will be identified by their total cationic charge value, e.g., [+8], [+16], etc.

Data are expressed as a mean ±1 SD. Statistical analysis using linear regression for determination of correlation coefficients, and analysis of variance (ANOVA) or unpaired two-way Student's t-test; $p<0.05$ was accepted as statistically significant.

Coagulation and Hematologic Studies

Anticoagulation reversal was assessed by a number of standard coagulation tests performed upon samples of venous blood: activated clotting time (ACT), prothrombin time (PT), activated partial thromboplastin time (aPTT), thrombin clotting time (TCT), heparin concentration by assay for FXa inhibitory activity (FXa), white cell count (WBC), and platelet counts (PLT). Measurements were made 3 minutes prior to heparin reversal (baseline) and 3 minutes and 30 minutes post-administration of the heparin reversal agent. Reversal of heparin anticoagulation, expressed as the percent change, was calculated and reported in Table 2 hereinbelow. The "Heparin" row sets forth the observed reversal as a consequence of expected heparin metabolism or degradation alone.

[+21] and [protamine +21], which resolved by about 30 minutes. Despite this trend, a linear correlation between peptide charge and degree of thrombocytopenia at 3 minutes was not observed. Analysis of change in white cell count at 3 and 30 minutes post-reversal also revealed no significant correlation with peptide charge.

Application of linear regression analysis to the data of Table 2 revealed a strong correlation between the percent reversal of heparin anticoagulation and peptide total cationic charge as shown in Table 3. Correlation coefficients relating coagulation studies to charge were generated on percent reversal data corrected for expected percent reversal due to heparin metabolism.

TABLE 3

CORRELATION OF TOTAL
CATIONIC CHARGE TO HEPARIN REVERSAL AS
MEASURED BY SELECTED COAGULATION STUDIES

|      | 3 min   | 30 min  |
| ---- | ------- | ------- |
| ACT  | 0.97+   | 0.99+   |
| PT   | 0.98+   | 0.87*   |
| aPTT | 0.99+   | 0.78    |
| TCT  | 0.84*   | 0.85*   |
| FXa  | 0.87*   | 0.85*   |
| FIIa | 0.79**  | —       |

*$p < 0.05$
+$p < 0.01$
**$p = 0.06$

The ability to reverse heparin as evaluated by these coagulation studies follows a linear relationship except for TCT and FIIa. Minimal TCT and FIIa reversal was noted for the peptide analogs having total cationic charge in the range

TABLE 2

PERCENT REVERSAL OF HEPARIN ANTICOAGULATION
BY VARIANT PEPTIDES AND PROTAMINE

|            | ACT   |        | PT    |        | APTT  |        | TCT   |        | FXa   |        | FNa   |
| ---------- | ----- | ------ | ----- | ------ | ----- | ------ | ----- | ------ | ----- | ------ | ----- |
| Charge     | 3 min | 30 min | 3 min | 30 min | 3 min | 30 min | 3 min | 30 min | 3 min | 30 min | 3 min |
| Heparin    | 4     | 41     | 5     | 46     | 12    | 66     | 0     | 0      | 3     | 8      | 6     |
| [+8]       | 7     | 37     | 21    | 50     | 0     | 50     | 0     | 0      | -1    | 9      | 8     |
| [+16]      | 54    | 65     | 73    | 59     | 58    | 56     | 0     | 0      | 23    | 42     | 8     |
| [+18]      | 81    | 82     | 74    | 91     | 79    | 80     | 75    | 57     | 60    | 51     | 41    |
| [+20]      | 92    | 87     | 83    | 80     | 91    | 91     | 109   | 92     | 83    | 70     | 79    |
| [+211]     | 81    | 85     | 97    | 93     | 88    | 85     | 91    | 79     | 55    | 49     | 59    |
| Protamine [+21] | 102 | 90 | 84    | 88     | 100   | 127    | 101   | 100    | 101   | 96     | 102   |

Figure 1B:
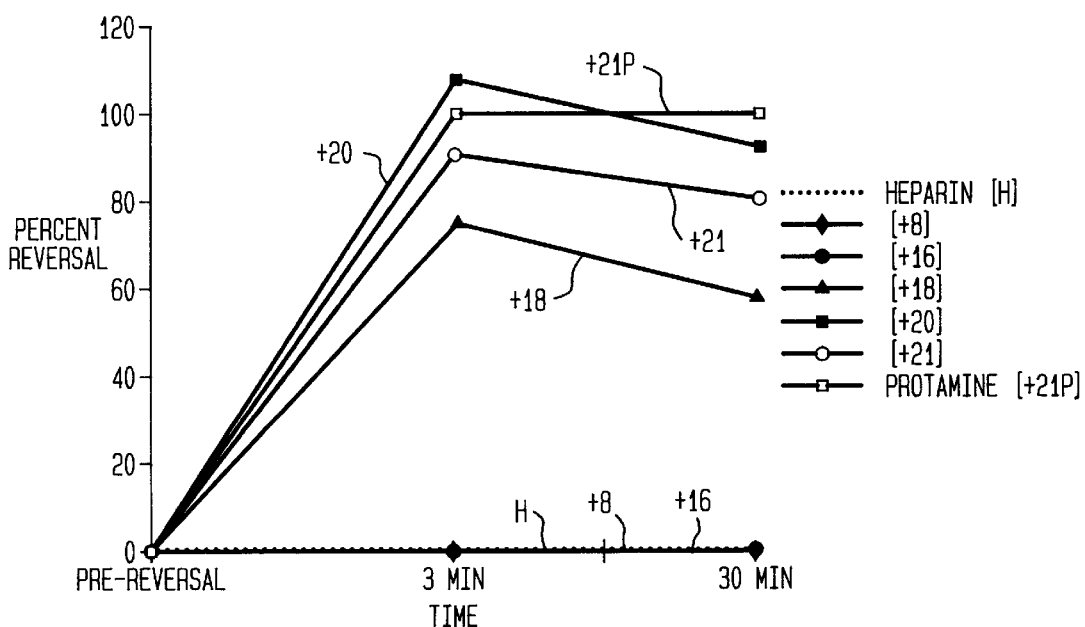
Figure 1C:
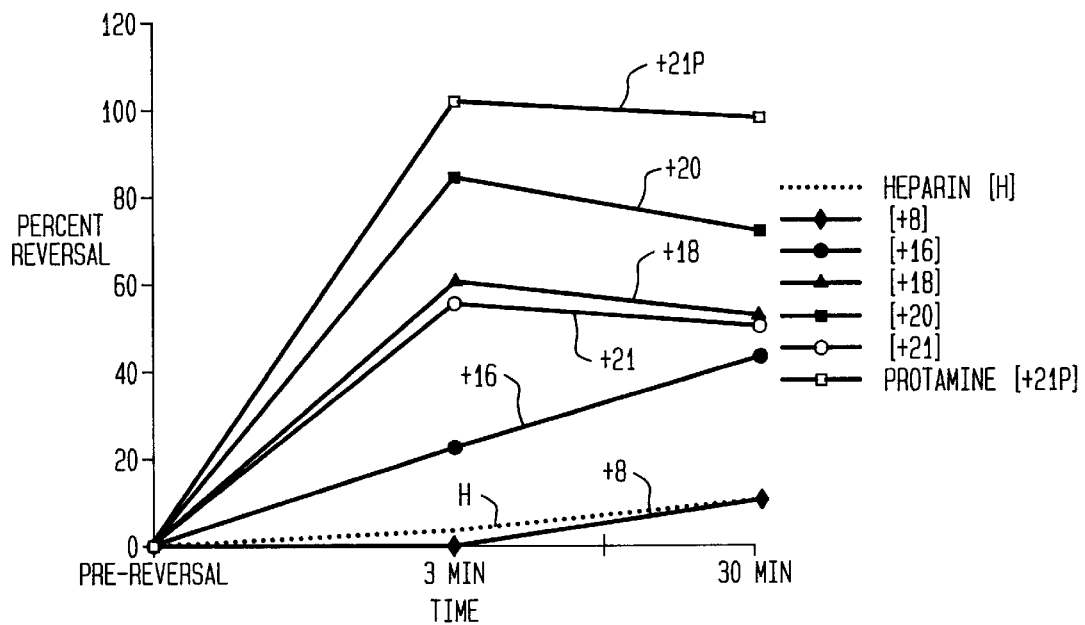
Figure 1D:
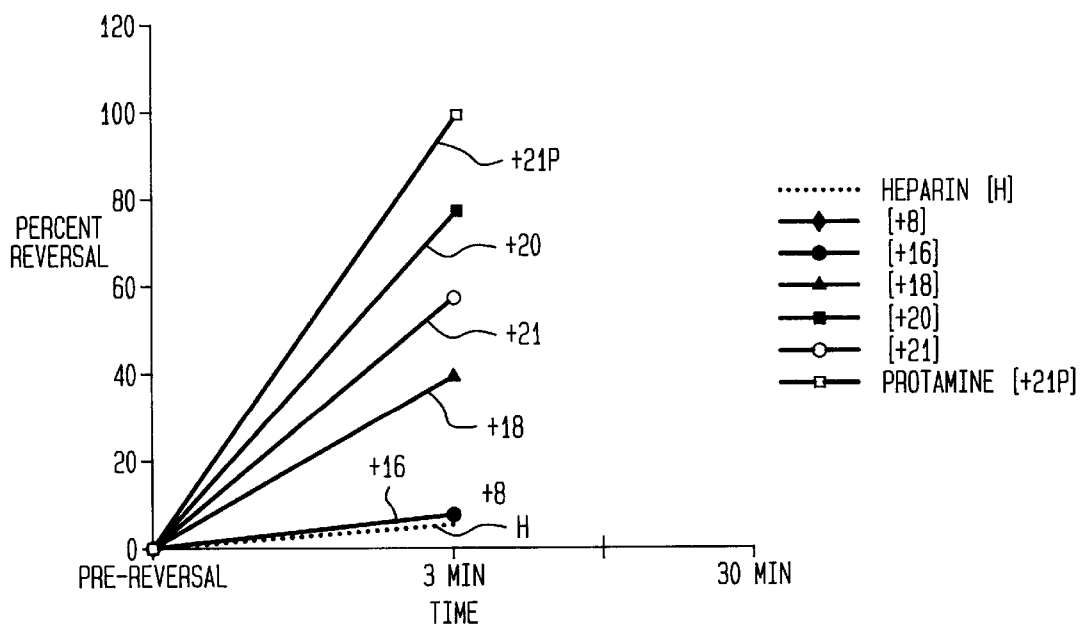

FIG. 1a through FIG. 1d are graphical representations of the heparin anticoagulation activities reported in Table 2. More specifically, FIG. 1a shows activated clotting time (ACT), FIG. 1b shows thrombin clotting time (TCT), FIG. 1c shows Heparin Antifactor Xa Activity, and FIG. 1d shows Heparin Antifactor IIa Activity. Referring to the figures, the [+18] peptide produced a modest amount of reversal of these parameters. Interestingly, [+16], while producing 54% ACT, 58% aPTT, and 23% FXa reversal resulted in no TCT or FIIa reversal above that expected by heparin degradation alone. This finding is noteworthy in that both TCT and FIIa assays measure only the thrombin-dependent portion of the coagulation cascade and, therefore, only the anti-IIa effects of heparin anticoagulation.

Analysis of platelet counts at 3 minutes post-reversal reveals thrombocytopenia with the peptides [+18], [+20], of [+8] to [+16]. Kinetic studies indicated that the H:AT-III inhibition complex binds to factor IIa with 25 times greater affinity than to factor Xa ($K_D(M)$ of $8\times10^{-6}$ and $2\times10^{-4}$, respectively). Thus, factor IIa may require more positive charge to remove it from the complex. This could explain the observed ability of the [+16] charged peptide to produce partial reversal of ACT, aPTT, and FXa, while producing essentially no reversal of either TCT or FIIa. In addition, kinetic studies have suggested that potentiation of AT-III's anti-IIa effect involves simultaneous binding between heparin and both AT-III and IIa.

Hemodynamic Studies

Hemodynamic studies were conducted by measuring mean arterial pressure (MAP), heart rate (HR), and maximum percent changes in cardiac output (CO) and systemic oxygen consumption ($VO_2$). The results of the hemodynamic studies are shown below in Table 4. Total peptide charge was correlated with observed decreases in MAP, CO and $VO_2$, but not HR.

TABLE 4

EFFECT OF PEPTIDE VARIANTS AND PROTAMINE ON SELECTED HEMODYNAMIC PARAMETERS

| Charge | ΔMAP | ΔCO | ΔVO₂ | ΔHR |
|---|---|---|---|---|
| [+8] | −1 | −8 | −8 | −9 |
| [+16] | −3 | −13 | −10 | −10 |
| [+18] | −31 | −41 | −34 | −17 |
| [+20] | −31 | −40 | −31 | −38 |
| [+21] | −35 | −44 | −38 | −21 |
| protamine [+21] | −34 | −38 | −35 | −29 |

Referring to Table 4, the average maximum decline in MAP in the first five minutes after peptide administration increased with increasing charge. Maximum decreases in MAP, CO and $VO_2$ correlated with total peptide charge with R values of 0.87, 0.87, and 0.86, respectively (significance= $p \leq 0.05$). Further, a trend towards decreasing HR with increasing peptide charge was found but did not achieve significance.

Figure 2A:
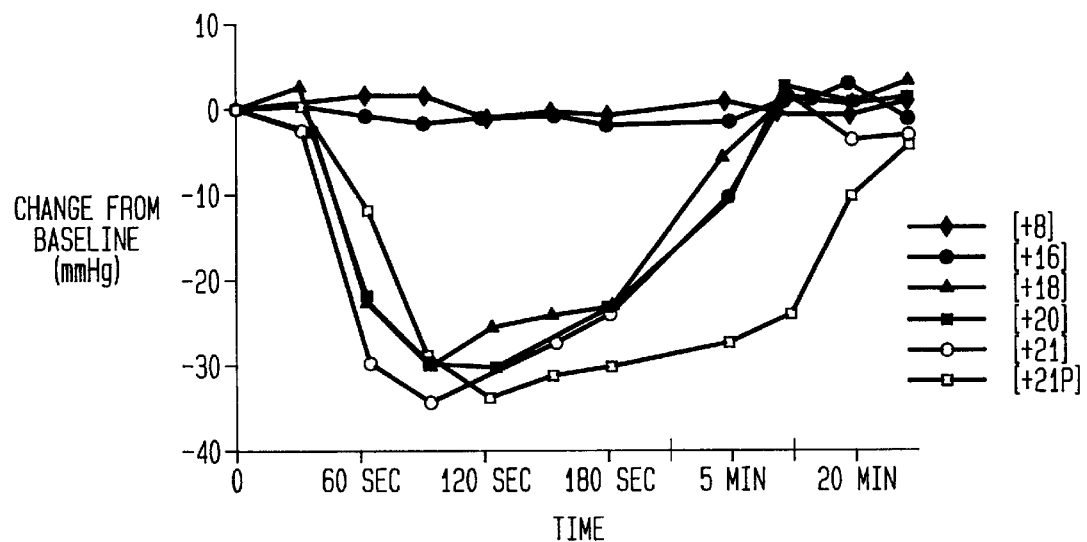
FIG. 2a and FIG. 2b are graphical representations of mean arterial blood pressure and cardiac output changes observed in an in vivo dog model following administration of protamine and selected synthetic protamine-like peptide analogs of the present invention. The data are expressed as percent change from baseline and are plotted against time.
Figure 2B:
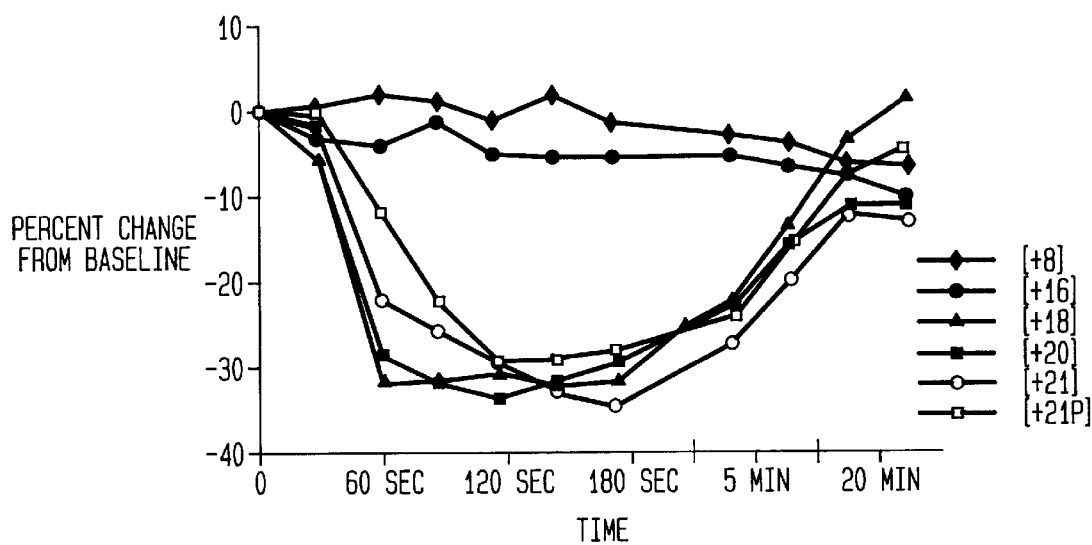

Referring to FIG. 2, the hemodynamic effects followed the same course and pattern for all peptides studied having a positive charge of greater than [+18]. This paralleled the typical response observed for protamine and differed only in the magnitude of hemodynamic changes. FIG. 2a is a classical depiction of the mean arterial pressure plotted as the change from baseline in mm Hg versus time. FIG. 2b is the cardiac output changes from baseline plotted versus time in percent change.

Total toxicity scores (TTS) were developed that reflected maximum declines in each of four parameters (MAP, CO, $VO_2$ and HR) over the first 5 minutes after reversal, the latter being the time of expected greatest adverse hemodynamic effect. The maximum changes occurring in an individual dog over the first 5 minutes were divided by the standard deviation derived from the entire group of tested animals and the four scores were added, resulting in a TTS for each individual dog. The TTS values for each dog were then summed to obtain an average TTS and SD for each peptide studied.

Figure 3:
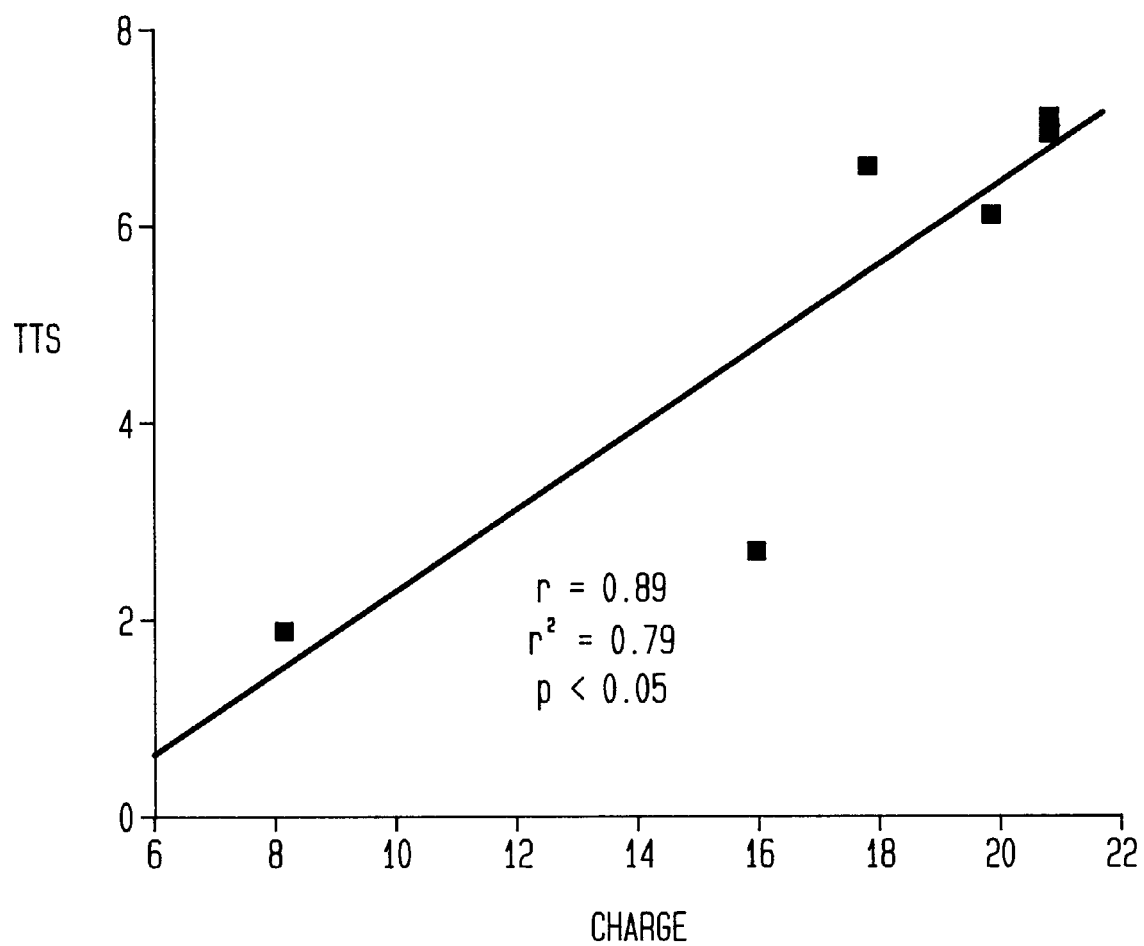
FIG. 3 is a graphical representation of total toxicity scores of selected synthetic protamine-like peptide analogs of the present invention plotted against total cationic charge of the peptide analog.

FIG. 3 is a graphical depiction of the correlation of total toxicity scores to peptide charges. Referring to FIG. 3, the magnitude of the average TTS±SD (expressed as a negative value, i.e., the more negative, the more toxic) was greater with increasing charge: −1.9±1.1[+8], −2.7±0.8[+16], −6.6±3.3[+18], −6.1±3.5[+20], −6.9±3.8 [+21], and −7.0±5.2 [protamine, +21]. There is a strong correlation between TTS and total cationic charge (R=0.89, p<0.05).

While peptides of [+14] charge were not used to generate the data reported in connection with the in vivo canine studies described hereinabove, other studies were conducted which demonstrated that the [+14] charged peptides had an effect on anticoagulation tests which was intermediate to that of the [+8] and [+16] peptides. The toxicity of the [+14] peptides was equal to or better than the toxicity of the [+16] peptide.

To summarize, the studies confirm that in vivo heparin reversal depends on the availability of positive charges on the molecules. Moreover, these positive charges do not have to be contributed by arginine. Increasing positive charge increases the ability of the synthetic protamine-like peptide to reverse heparin anticoagulation. Although nearly complete reversal of the anticoagulation effects of heparin is achieved with peptides having a charge of [+20] or [+21], the peptide with [+8] charge was not capable of effect heparin reversal. However, reducing the total positive charge from [+21] results in a lower toxicity. There is a difference in toxicity between a peptide with a total cationic charge of [+16] and those charged with [+18] or greater. Thus, peptides of total cationic charge ranging from [+14] to [+18] exhibit a partial ability to reverse the effects of heparin, but have reduced toxicity.

II. Studies on the Reversal of the Anticoagulation Effects of Low Molecular Weight Heparins The ability of the protamine-like peptides of the present invention to reverse the anticoagulation effects of LMWH was assessed in a canine model using model compounds of charges between [+16] and [+18] as set forth in Table 5 hereinbelow. Standard n-protamine was used as a control.

TABLE 5

| Amino Acid Sequence | Seq. Listing ID No. | Total Cationic Charge |
|---|---|---|
| (1) P(AK₂A₂K₂)₄ | 15 | [+16]* |
| (2) acetyl-P(AK₂A₂K₂)₄-amide | 15 | [+16B] |
| (3) acetyl-PAK₂(AK₂A₂K₂)₃AK₂-amide | 1 | [+16B]* |
| (4) acetyl-E(AK₂A₂K₂)₄-amide | 3 | [+16BE] |
| (5) PK(K₂A₂K₂A)₃K₂AK₃ | 16 | [+18]* |
| (6) acetyl-PA(K₂A₂K₂A)₄K₂-amide | 2 | [+18B]* |
| (7) acetyl-EA₂(K₂A₂K₂A)₄K₂amide | 4 | [+18BE] |
| (8) PR₄S₃RPVR₅PRVSR₆G₂R₄ (n-protamine) | 14 | [+21]* |
| (9) acetyl-EA—(R₂A₂R₂A)₄R₂GRGDSPA-amide | 5 | [+18RGD] |

In these embodiments, the aminoacyl connecting residues of n-protamine were replaced with alanine residues in an effort to increase stability of alpha-helix formation on binding to LMWH. The peptide length was made constant at 29 amino acids, and positive charge was calculated by counting lysine (K) residues. In the embodiments labeled "B," e.g., [+16B] and [+18B], the peptide has been amidated at the C-terminus and acetylated at the N-terminus to mitigate against in vivo degradation by carboxypeptidases and amino-peptidases, respectively. In embodiments labeled "BE," the non-α-helix forming amino acid proline has been replaced with α-helix forming glutamic acid. The "B" and "BE" compounds have peptide lengths which reflect the number of amino acid residues necessary in order to maintain optimal spacing for alpha-helix formation on binding to heparin. The acetyl and amide moieties also contribute to alpha helix stability by increasing the helical dipole moment.

The protamine-like peptides used in these studies were synthesized on an automated peptide synthesizer using FMOC-amino acids (Applied Biosystems Model 431 synthesizer, Applied Biosystems, Foster City, Calif.) as described hereinabove. In the specific illustrative embodiments set forth in Table 5, the peptides were synthesized in the automated synthesizer on preloaded Wang resins or on RINK resin with 9-fluorenylmethoxy-carbonyl amino acid derivatives. The hydroxybenzotriazolyl esters of the 9fluorenylmethoxycarbonyl-amino acids were formed using 2-(1 H benzotriazol-1-yl)-1,1,3,3-tetramethyluronium hexafluorophosphate as an activation agent. Coupling and deprotection of the nascent peptide chains were accomplished under standard conditions for the synthesizer (FastMOC cycles). Cleavage and final deprotection were in 90% trifluoroacetic acid containing 5% ethanedithiol, 2.5% thioanisole, and 2.5% anisole for 2 hours at room temperature. The peptides were precipitated from the trifluoroacetic acid by 20 volumes of diethylether at −20° C. Once synthesized, the peptides were purified by reversed-phase high performance liquid chromatography (HPLC) on a 2"×25 cm preparative reversed-phase column (Rainin, Dynamax). The flow rate was 17 ml/min. and the gradient was from 5% to 60% acetonitrile in 90 minutes. In some instances, the peptides were subsequently desalted on Sephadex G15 (Pharmacia, Piscataway, N.J.) gel filtration columns equilibrated with 1N acetic acid. Each purified peptide was characterized by amino acid analysis, analytical reversed-phase HPLC, and mass spectroscopy to confirm purity before use. Inclusion of norleucine as an internal standard allowed accurate assessment of peptide concentration.

in vivo Canine Studies

Seven female dogs (mean weight 12.3kg) received intravenous LMWH (LHN-1, Logiparin, Novo, Denmark; 150 IU/kg factor Xa activity) followed by reversal with commercial salmine protamine (n-protamine purchased from Eli Lilly, Indianapolis, Ind., 1.5 mg/kg (100 IU/mg) IV) or one of the variants identified hereinabove at Table 5 with an asterisk after 30 minutes.

Coagulation and Hematologic Studies

Anticoagulation reversal was assessed by a number of standard coagulation tests performed upon samples of venous blood: activated clotting time (ACT), heparin concentration by assay for FXa inhibitory activity (FXa), thrombin clotting time (TCT), and heparin concentration by assay for FIIa inhibitory activity (FIIa). Measurements were made 3 minutes prior to heparin reversal (baseline) and 3 minutes, 10 minutes, and 30 minutes post-administration of the heparin reversal agent. Reversal of LMWH anticoagulation, expressed as the percent change, was calculated and reported in Table 6 hereinbelow. Changes in LMWH anticoagulation occurring from metabolism alone were determined from measurements obtained on a group of five dogs which were not given a reversal agent. The coagulation data were corrected for naturally occurring metabolism.

TABLE 6

PERCENT REVERSAL OF LOW MOLECULAR WEIGHT HEPARIN ANTICOAGULATION BY VARIANT PEPTIDES AND PROTAMINE

| | ACT | | | FXa | | | TCT | | | FNa | | |
|---|---|---|---|---|---|---|---|---|---|---|---|---|
| Charge | 3 min | 10 min | 30 min | 3 min | 10 min | 30 min | 3 min | 10 min | 30 min | 3 min | 10 min | 30 min |
| [+16] | 26 | 55 | 78 | 25 | 19 | 29 | 66 | 32 | 50 | 43 | 7 | 44 |
| [+16B] | 62 | 69 | 80 | 48 | 32 | 43 | 97 | 81 | 87 | 77 | — | 69 |
| [+18] | 49 | 52 | 61 | 21 | 17 | 24 | 91 | 67 | 64 | 36 | 24 | 46 |
| [+18B] | 87 | 93 | 102 | 64 | 34 | 52 | 99 | 95 | 96 | 96 | 72 | 74 |
| Protamine [+21] | 99 | 88 | 82 | 63 | 45 | 44 | 100 | 98 | 96 | 99 | — | 86 |

In addition to the measurements reported on Table 6, studies were conducted to measure the activated partial thromboplastin time (aPTT), platelet count, and white blood cell count. There was little to no reversal of aPTT values by the [+16] and [+18] variants, and in fact, both produced a paradoxical increase in aPTT at 3 minutes. However, the [+18B] variant produced greater aPTT reversal than protamine at the 3, 10 and 30 minute measurements (64%, 95%, and 93%, respectively, as compared to 50%, 83%, and 78%, respectively, for protamine). No decrease in thrombocytopenia was observed for the [+18B] variant which has a mean decline in platelet count of −56% as compared to the mean decline in platelet count of −43% observed for protamine. However, the [+16] and [+18] variants exhibited a substantial decrease in thrombocytopenia with mean declines in platelet count of −24% and −8%, respectively. The decline in white blood cell count was found to be the greatest for the [+18B] variant.

The data demonstrate that the protamine-like peptides of the present invention effectively reverse the effects of LMWH. In the case of [+18B], reversal occurs to a degree approaching the efficacy of standard protamine. However, the variants of the present invention are much less toxic than protamine, as will be described hereinbelow in connection with their total toxicity score (TTS).

Hemodynamic Studies

Hemodynamic studies were conducted by measuring mean arterial pressure (MAP) in mm Mercury, maximum percent changes in cardiac output (CO) and systemic oxygen consumption ($VO_2$), and heart rate (HR) in beats per minute. The results of the hemodynamic studies are shown below in Table 7. Measurements and calculations were made at baseline, before LMWH administration, 3 minutes before reversal, every 30 seconds for 5 minutes after reversal, and at 10, 20, and 30 minutes after reversal.

TABLE 7

EFFECT OF PEPTIDE VARIANTS AND PROTAMINE ON SELECTED
HEMODYNAMIC PARAMETERS FOLLOWING ADMINISTRATION
OF LOW MOLECULAR WEIGHT HEPARIN

| Charge | ΔMAP | ΔCO | ΔVO$_2$ | ΔHR |
|---|---|---|---|---|
| [+16] | −6 | −8 | −10 | −7 |
| [+16B] | −19 | −18 | −16 | −17 |
| [+18] | −1 | −3 | −4 | −1 |
| [+18B] | −10 | −18 | −12 | −9 |
| protamine [+21] | −32 | −32 | −26 | −18 |

In addition to the foregoing, maximum mean increases in pulmonary artery systolic (PAS) and diastolic (PAD) pressures following administration of protamine were +10 mm Mercury and +10 mm Mercury, respectively. All of the protamine-like peptides of the present invention were observed to produce greatly decreased responses for both PAS and PAD (+1 mm Mercury for the [+16] and [+18] variants and no increase for the [+16B] and [+18B] variants).

Total toxicity scores (TTS) were developed that reflected maximum declines in each of four parameters (MAP, CO, VO$_2$ and HR) over the first 5 minutes after reversal. The maximum changes occurring in an individual dog over the first 5 minutes were divided by the standard deviation derived from the entire group of tested animals and the four scores were added, resulting in a TTS for each individual dog. The TTS values for each dog were then summed to obtain an average TTS and SD for each peptide studied. The more negative the value of TTS, the more toxic the compound. The TTS for the protamine-like peptide variants of Table 5 are set forth in Table 8.

TABLE 8

| Charge | Total Toxicity Score |
|---|---|
| [+16] | −2.8 ± 2.0* |
| [+16B] | −4.27 ± 1.1 |
| [+18] | −1.3 ± 1.0** |
| [+18B] | −4.1 ± 1.6*** |
| [+21] n-protamine | −7.6 ± 4.8 |

*p < 0.05;
**p < 0.01;
***p = 0.084

Referring to Table 8, the [+16] and [+18] variants are significantly less toxic than protamine. While the [+16B] and [+18B] variants are also less toxic than protamine, the difference is not statistically significant. However, the efficacy of these variants, particularly [+18B], as shown in Tables 6 and 7, is substantially the same as, or better than, protamine in reversing the anticoagulation effects of LMWH. Moreover, the [+18B] variant was actually more effective than protamine by aPTT measurements.

Dose-response studies were conducted. A 50% less dose (1:2 versus 1:1 peptide to LMWH) of [+18B], for example, lowers TTS to about −1.62. Of course, the ability of the peptide to reverse the anticoagulation effects of the LMWH is lowered as well. However, a person of ordinary skill in the art can adjust the dose to achieve an acceptable level of reversal and to minimize toxicity.

The data clearly demonstrate that synthetic protamine-like peptides, in accordance with the present invention, reverse LMWH anticoagulation and are less toxic than protamine. Further, modification of the N- and C-termini to prevent in vivo degradation improves the efficacy of the synthetic protamine-like peptides in reversing the anticoagulation effects of LMWH to a level substantially equaling, and in some cases exceeding, the efficacy of protamine.

III. Additional Studies on the Reversal of the Anticoagulation Effects of Standard Heparin and Low Molecular Weight Heparin in vivo Canine Studies In addition to the foregoing, an experiment was designed to investigate the influence of the speed of administration of the anticoagulation-reversing agents.

Seven female dogs (mean weight 13 kg) received intravenous LMWH (LHN-1, Logiparin, Novo, Denmark; 150 IU/kg factor Xa activity) followed by reversal after 30 minutes with commercial salmine protamine (n-protamine purchased from Eli Lilly, Indianapolis, Ind., 1.5 mg/kg (100 IU/mg) IV) or one of the variants identified hereinabove at Table 5 as acetyl-PA(K$_2$ A$_2$ K$_2$A)$_4$ K$_2$-amide [+18B] (Sequence Listing ID No. 2) or acetyl-EA$_2$(K$_2$A$_2$K$_2$A)$_4$K$_2$-amide [+18BE](Sequence Listing ID No. 4). The anticoagulation-reversing agents were administered rapidly over 10 seconds to maximize hemodynamic effects or more slowly over a 3 minute interval. Changes in LMWH anticoagulation occurring from metabolism alone were determined in a separate group of dogs not given any reversal agent.

Coagulation and Hematologic Studies

Anticoagulation reversal was assessed by a number of standard coagulation tests performed upon samples of venous blood in the manner described hereinabove. Measurements were made 3 minutes prior to heparin reversal (baseline) and 3 minutes, 10 minutes, and 30 minutes post-administration of the heparin reversal agent. Reversal of LMWH anticoagulation, expressed as the percent change, was calculated and reported in Table 9 hereinbelow.

TABLE 9

PERCENT REVERSAL OF
LOW MOLECULAR WEIGHT HEPARIN ANTICOAGULATION BY
VARIANT PEPTIDES AND PROTAMINE
ADMINISTERED AT DIFFERENT RATES

| | ACT | | | FXa | | | TCT | | | FNa | | |
|---|---|---|---|---|---|---|---|---|---|---|---|---|
| Charge | 3 min | 10 min | 30 min | 3 min | 10 min | 30 min | 3 min | 10 min | 30 min | 3 min | 10 min | 30 min |
| [+18B] 10 sec | 87 | 87 | 98 | 64 | 34 | 52 | 99 | 95 | 100 | 95 | 72 | 74 |
| [+18BE] 10 sec | 65 | 78 | 81 | 73 | 51 | 59 | 100 | 95 | 95 | 99 | 83 | 79 |

TABLE 9-continued

PERCENT REVERSAL OF
LOW MOLECULAR WEIGHT HEPARIN ANTICOAGULATION BY
VARIANT PEPTIDES AND PROTAMINE
ADMINISTERED AT DIFFERENT RATES

| Charge | ACT | | | FXa | | | TCT | | | FNa | | |
|---|---|---|---|---|---|---|---|---|---|---|---|---|
| | 3 min | 10 min | 30 min | 3 min | 10 min | 30 min | 3 min | 10 min | 30 min | 3 min | 10 min | 30 min |
| [+18BE] 3min | 89 | 95 | 97 | 91 | 68 | 60 | 100 | 100 | 99 | 94 | 99 | 84 |
| Protamine 10 sec | 96 | 83 | 78 | 63 | 45 | 44 | 99 | 98 | 96 | 96 | — | 86 |
| Protamine 3 min | 99 | 87 | 80 | 68 | 53 | 45 | 100 | 99 | 98 | 99 | 98 | 92 |

All peptide variants had excellent anticoagulation reversal efficacy. However, compound [+18BE] administered over a 3 minute period had equal, if not greater, efficacy than protamine [+21] as demonstrated by antifactor Xa reversal. At 3 minutes post-administration, compound [+18BE] was significantly superior to protamine administered over a 10 second interval (p<0.01) or over a 3 minute interval (p<0.05).

Maximal thrombocytopenia for the compounds in Table 9 was: −56% for [+18B] (10 sec); −44% for [+18BE] (10 sec); −49% for [+18BE] (3 min); −43% for [+21] (10 sec); and −32% for protamine [+21] (3 min). Nevertheless, thrombocytopenia had reverted to −8% by 10 minutes for [+18BE] and the platelet count had rebounded +35% by 30 minutes in [+18BE] administered over a 3 minute interval. Similar return to above baseline was observed for [+18BE] administered over 10 seconds.

In selected animals, bleeding time was determined for protamine[+21] and [+18BE] given over a 3 minute interval. The bleeding time never surpassed 8 minutes despite the large percent drop in platelet count. Maximal declines in leukocyte count were: −21% for [+18B] (10 sec); −1% for [+18BE] (10 sec); −7% for [+18BE] (3 min); −3% for protamine [+21] (10 sec); and −26% for protamine [+21] (3 min). There were no significant declines in either platelet or white blood cell count as ascertained by ANOVA between any of the foregoing groups.

Hemodynamic Studies

Hemodynamic studies were conducted by measuring mean arterial pressure (MAP) in mm Mercury, maximum percent changes in cardiac output (CO) and systemic oxygen consumption ($VO_2$), and heart rate (HR) in beats per minute. The results of the hemodynamic studies are shown below in Table 10. Measurements and calculations were made at baseline, before LMWH administration, 3 minutes before reversal, every 30 seconds for 5 minutes after reversal, and at 10, 20, and 30 minutes after reversal.

TABLE 10

EFFECT OF PEPTIDE VARIANTS AND PROTAMINE
ADMINISTERED AT DIFFERENT RATES ON SELECTED
HEMODYNAMIC PARAMETERS FOLLOWING ADMINISTRATION
OF LOW MOLECULAR WEIGHT HEPARIN

| Charge | ΔMAP | ΔCO | $ΔVO_2$ | ΔHr |
|---|---|---|---|---|
| [+18B] 10 sec | −10 | −18 | −12 | −9 |
| [+18BE] 10 sec | −8 | −11 | −12 | −13 |
| [+18BE] 3 min | 0 | −7 | −10 | −5 |
| protamine [+21] 10 sec | −32 | −32 | −26 | −18 |
| protamine [+21] 3 min | −18 | −28 | −23 | −36 |

None of the peptide variants caused any increase in pulmonary artery pressure as compared to protamine irrespective of whether administered over a 10 second interval or a 3 minute interval.

TTS were developed that reflected maximum declines in each of four parameters (MAP, CO, $VO_2$ and HR) over the first 5 minutes after reversal in the same manner as described hereinabove. The TTS for the protamine-like peptide variants used in this experiment are set forth in Table 11.

TABLE 11

TOTAL TOXICITY SCORES FOR PEPTIDE VARIANTS
AND PROTAMINE ADMINISTERED AT DIFFERENT RATES

| Charge | Total Toxicity Score |
|---|---|
| [+18B] 10 sec | −3.1 ± 1.5 |
| [+18BE] 10 sec | −2.3 ± 3.6 |
| [+18BE] 3min | −2.2 ± 1.7 |
| n-protamine [+21] 10 sec | −6.4 ± 3.8 |
| n-protamine [+21] 3 min | −7.2 ± 3.5 |

The peptide variant [+18BE] administered over a 3 minute interval was significantly less toxic than protamine when administered over a 3 minute interval (p<0.01) or protamine administered over a 10 second interval (p=0.02). Even when administered over a 10 second period, peptide variant [+18BE] was nearly significantly less toxic than protamine administered over a 10 second period (p=0.065). Moreover, peptide variant [+18BE] exhibits excellent reversal efficacy with antifactor Xa activity as high as 91%. This is in comparison to 68% for protamine [+21] when administered over a 3 minute interval (p<0.05). Most importantly, however, reversal efficacy remained at a level comparable to standard protamine at 10 minutes and 30 minutes post-administration for both speeds of administration.

In addition to efficacy with respect to LMWH, peptide variant [+18BE] was administered over either a 10 second interval or a 3 minute to dogs (n=7) which had been anticoagulated with standard heparin. The results are shown in Table 12 at 3 minutes, 10 minutes, and 30 minutes post-administration:

TABLE 12

PERCENT REVERSAL OF STANDARD HEPARIN
ANTICOAGULATION BY PEPTIDE [+18BE]
ADMINISTERED AT DIFFERENT RATES

| Charge | ACT | | | FXa | | | TCT | | | FNa | | |
|---|---|---|---|---|---|---|---|---|---|---|---|---|
| | 3 min | 10 min | 30 min | 3 min | 10 min | 30 min | 3 min | 10 min | 30 min | 3 min | 10 min | 30 min |
| [+18BE] 10 sec | 95 | 98 | 96 | 99 | 95 | 97 | 100 | 98 | 98 | 100 | 99 | 100 |
| [+18BE] 3 min | 98 | 98 | 98 | 99 | 97 | 96 | 100 | 100 | 100 | 99 | 98 | 99 |

Hemodynamic studies were conducted by measuring mean arterial pressure (MAP) in mm Mercury, maximum percent changes in cardiac output (CO) and systemic oxygen consumption ($VO_2$), and heart rate (HR) in beats per minute. The results of the hemodynamic studies are shown below in Table 13. Measurements and calculations were made at baseline, before LMWH administration, 3 minutes before reversal, every 30 seconds for 5 minutes after reversal.

TABLE 13

EFFECT OF PEPTIDE [+18BE] ADMINISTERED
AT DIFFERENT RATES ON SELECTED
HEMODYNAMIC PARAMETERS
FOLLOWING ADMINISTRATION OF STANDARD HEPARIN

| Charge | ΔMAP | ΔCO | $\Delta VO_2$ | ΔHR |
|---|---|---|---|---|
| [+18BE] 10 sec | −1 | −9 | −9 | −8 |
| [+18BE] 3 min | 1 | −17 | −10 | −8 |

TTS were developed that reflected maximum declines in each of four parameters (MAP, CO, $VO_2$ and HR) over the first 5 minutes after reversal in the same manner as described hereinabove. The TTS for peptide variant [+18BE], administered over 10 second and 3 minute intervals, to offset the anticoagulation effects of standard heparin are set forth in Table 14.

TABLE 14

TOTAL TOXICITY SCORES FOR PEPTIDE [+18BE]
AND PROTAMINE ADMINISTERED AT DIFFERENT RATES

| Charge | Total Toxicity Score |
|---|---|
| [+18BE] 10 sec | −2.14 ± 0.40* |

TABLE 14-continued

TOTAL TOXICITY SCORES FOR PEPTIDE [+18BE]
AND PROTAMINE ADMINISTERED AT DIFFERENT RATES

| Charge | Total Toxicity Score |
|---|---|
| [+18BE] 3 min | −1.96 ± 0.55** |
| n-protamine (+21) 10 sec | −7.1 ± 4.63 |

TABLE 14-continued

TOTAL TOXICITY SCORES FOR PEPTIDE [+18BE]
AND PROTAMINE ADMINISTERED AT DIFFERENT RATES

| Charge | Total Toxicity Score |
|---|---|
| n-protamine [+21] 3 min | −5.66 ± 4.04 |

*$p < 0.05$;
**$p < 0.05$ in comparison to protamine

The data presented hereinabove demonstrates that peptide variant [+18BE] is a safe and effective compound for reversal of both LMWH and standard heparin.

IV. Additional Embodiments Having the Ability to Reverse the Anticoagulation Effects of Standard Heparin and Low Molecular Weight Heparin In a still further embodiment of the invention, cell adhesion ligands of the type which are known to bind to cell matrices, such as the fibronectin-receptor ligand "RGD" or the laminin-receptor ligand "YIGSR (Sequence Listing ID No. 18)," are included in backbone structure of the protamine analogs of the present invention to further reduce toxicity. Although not wishing to be bound by theory, the presence of cell adhesion ligands reduces the level of free synthetic protamine-like peptides in circulation thereby reducing toxicity. It is believed that inclusion of an RGD sequence, for example, in the sequence comprising the protamine analogs allows the protamine analog to bind to receptors on cell surfaces while still being exposed to the serum for interaction with heparin and/or LMWH. Binding to the receptors immobilizes the protamine analog and thereby reduces the concentration of free compound in the bloodstream. The RGD sequence is particularly advantageous for this purpose since the RGD receptor is relatively widespread so that the binding capacity will be quite high. It is likely that this same approach, i.e., attachment of a cell adhesion ligand, will work for other drugs that target components of the circulatory system, so as to provide a reservoir of immobilized drug and lower the concentration of free compound.

In an illustrative embodiment of the invention, one or more fibronectin-receptor ligands, "RGD," are incorporated into the protamine analogs of the present invention. The RGD sequence(s) may be in the vicinity of the N- and/or C-termini, or within the backbone structure of a protamine-like peptide sequence formulated in accordance with the principles of the present invention as set forth hereinabove. It should be noted, that in embodiments incorporating cell adhesion ligands, it is possible to provide protamine-like peptide variants having greater positive charge and less toxicity.

In a specific example of this advantageous embodiment of the invention, a protamine-like peptide analog has the molecular formula Acetyl-EA$(R_2A_2R_2A)_4R_2$GRGDSPA-amide, herein designated [+18RGD] (Sequence Listen ID No. 5). Compound [+18RGD] has a backbone sequence similar to compound [+18BE] described hereinabove. In this particular embodiment, however, the lysines found in [+18BE] are replaced by arginines and an RGD sequence, specifically GRGDSPA (residues 33–39 of Sequence Listing ID No. 5), occurs at the C-terminus end. Compound [+18RGD] may be made in accordance with the procedures specified above and in a manner known to persons of ordinary skill in the art.

in vivo Canine Studies

Seven female dogs (mean weight 15–20kg) received intravenous standard, unfractionated heparin (150 IU/kg IV) or LMWH (Enoxaparin, Rhone-Poulac, France; 100 IU/kg factor Xa activity) followed by reversal with commercial salmine protamine (n-protamine purchased from Eli Lilly, Indianapolis, Ind., 1.5 mg/kg (100 IU/mg) IV) or an anticoagulation-reversing agent which is a protamine-like peptide variant identified hereinbelow. In these studies, the anticoagulation-reversing agents were administered over a 10 second interval to maximize the hemodynamic effects.

The variants used in these studies were [+18BE] and [+18RGD]. For comparative purposes, a compound incorporating the KDEL sequence which is known to bind to receptors found in the endoplasmic reticulum, as well as receptors on the surface of other liver cells, was synthesized and administered to dogs in the studies reported herein. The molecular formula of this compound is: acetyl-EA $(R_2A_2R_2A)_4R_2$GVKDEL, designated [+18KDEL] (Sequence Listing ID No. 17). The C-terminus of [+KDEL] is a free carboxylate.

Coagulation and Hematologic Studies

Figure 4A:
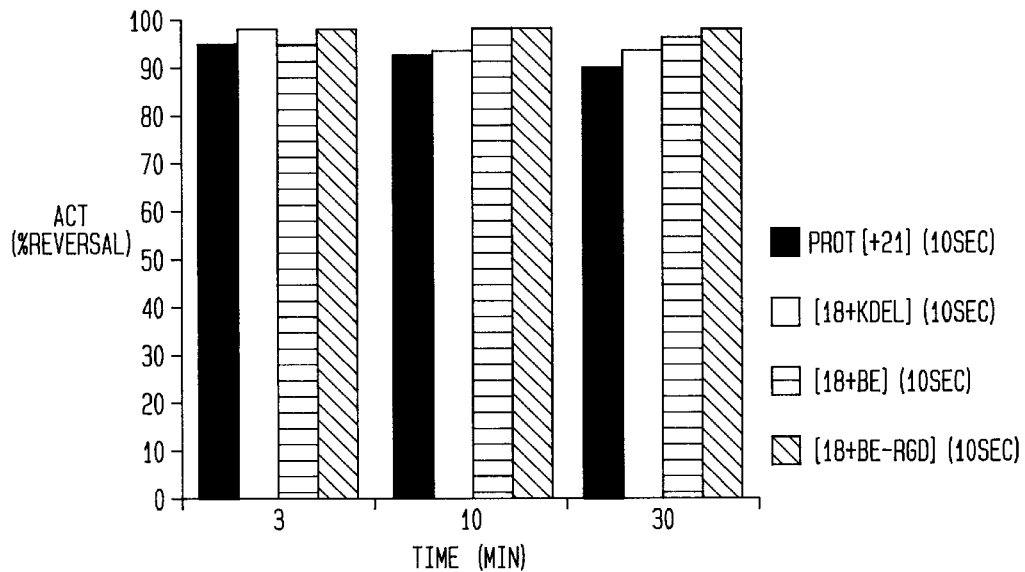
FIG. 4a through FIG. 4d are graphical representations of heparin anticoagulation activities achieved by n-protamine (Protamine [+21]) and selected synthetic protamine-like peptide analogs, including an analog including a cell adhesion ligand, plotted as a percent of reversal against time in minutes, more specifically.
Figure 4B:
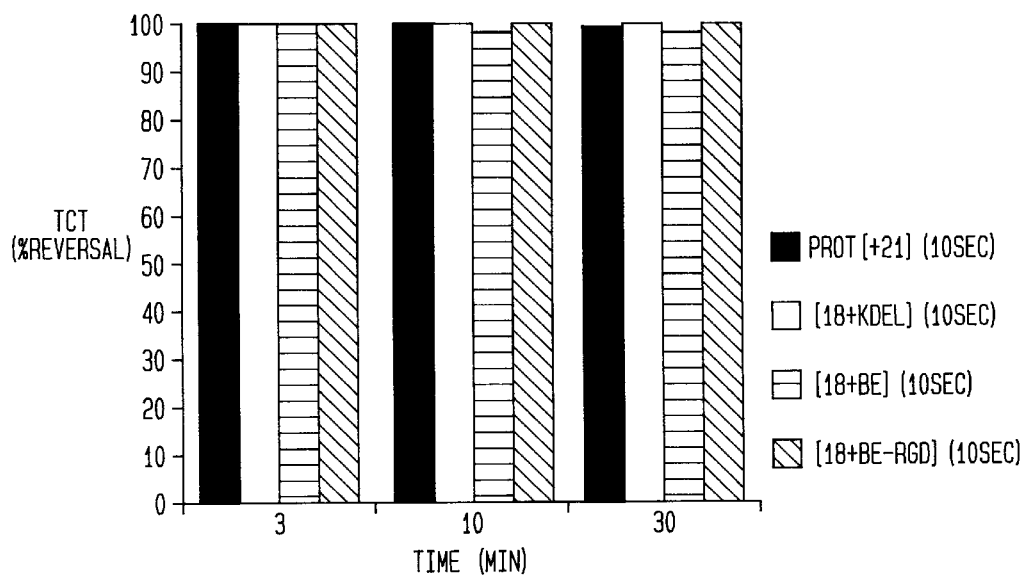
Figure 4C:
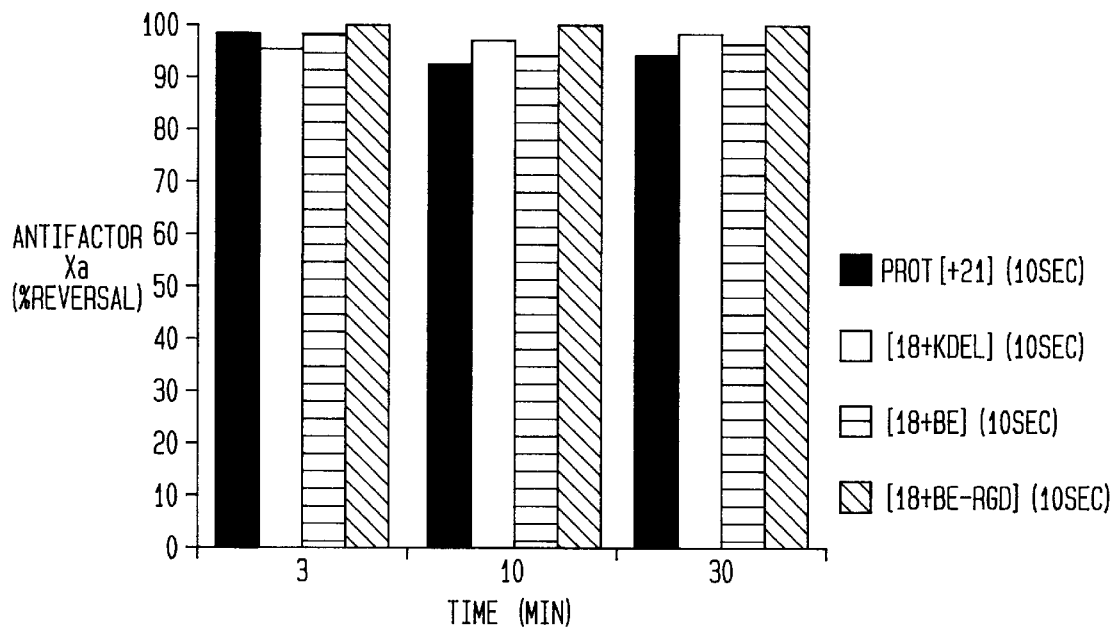
Figure 4D:
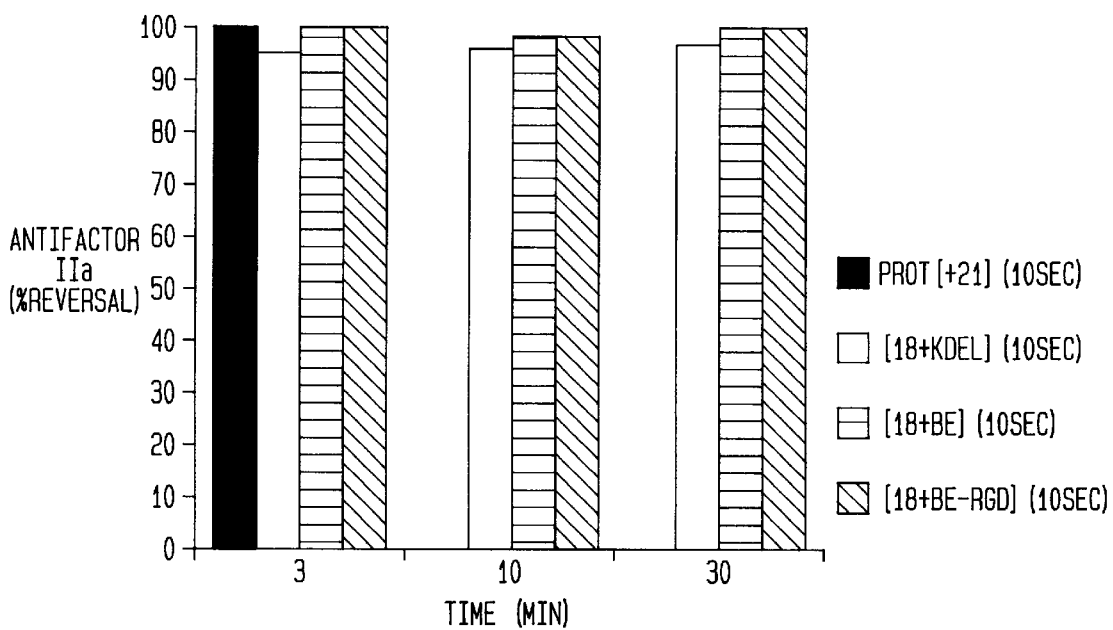

Anticoagulation reversal was assessed by a number of standard coagulation tests performed upon samples of venous blood in the manner described hereinabove. Measurements were made 3 minutes prior to heparin reversal (baseline) and 3 minutes, 10 minutes, and 30 minutes post-administration of the heparin reversal agent. FIG. 4a through FIG. 4d are graphical representations of heparin anticoagulation activities achieved by n-protamine (Protamine [+21]), and the synthetic protamine-like peptide analogs [+18BE], [+18RGD], and [+18KDEL] plotted as a percent of reversal against time in minutes, more specifically, FIG. 4a shows activated clotting time (ACT), FIG. 4b shows thrombin clotting time (TCT), FIG. 4c shows heparin antifactor Xa activity, and FIG. 4d shows heparin antifactor IIa activity. Referring to FIGS. 4a through 4d, compound [+18RGD] performs as well, or better, than n-protamine in the standard coagulation tests performed in these studies.

Hemodynamic studies were conducted by measuring mean blood pressure (Mean BP) in mm Mercury, maximum percent changes in cardiac output (CO) and systemic oxygen consumption ($VO_2$), and heart rate (HR) in beats per minute. The results of the hemodynamic studies are shown below in Table 15. Measurements and calculations were made at baseline, before administration of standard, unfractionated heparin, 3 minutes before reversal, every 30 seconds for 5 minutes after reversal.

TABLE 15

Maximum Hemodynamic Changes
5 Minutes after Administration of Heparin

|  | [+18BE] | [+18KDEL] | [+18RGD] | Prot[+21] |
|---|---|---|---|---|
| Mean BP (mm Mercury) | −1 | −5 | −2 | −31 |
| CO | −9% | −12% | −3% | −36% |
| $VO_2$ | −9% | −6% | −4% | −32% |
| HR (beats/min) | −8 | −14 | −3 | −27 |
| Platelet | −46% | −24% | −27% | −54% |
| Xa Reversal (3 min) | 99% | 97% | 100% | 99% |
| IIa Reversal (3 min) | 100% | 94% | 100% | 98% |

In addition to hemodynamic changes, Table 15 lists the percent change in platelet count following administration of n-protamine and the selected variants, as well as the factor Xa and factor IIa reversal, as a percent change at 3 minutes post administration of the compound. It should be noted that [+18RGD] produces greater reversal of antifactor Xa and IIa activity than n-protamine, but also has a significantly decreased impact on platelet count.

Total toxicity scores (TTS) were developed in accordance with the method described hereinabove that reflected maximum declines in each of four parameters (MAP, CO, $VO_2$ and HR) over the first 5 minutes after reversal. The TTS for the protamine-like peptide variants of Table 15 are set forth in Table 16.

TABLE 16

| Charge | Total Toxicity Score |
|---|---|
| [+18BE] | −2.41 ± 0.47 |
| [+18KDEL] | −3.53 ± 1.65 |
| [+18RGD] | −1.43 ± 0.61 |
| [+21] n-protamine | −8.02 ± 5.20 |

In performing statistics on these four compounds for standard unfractionated heparin, there was a significant difference between the [+18RGD] compound and all of the other listed compounds with p<0.01.

Figure 5A:
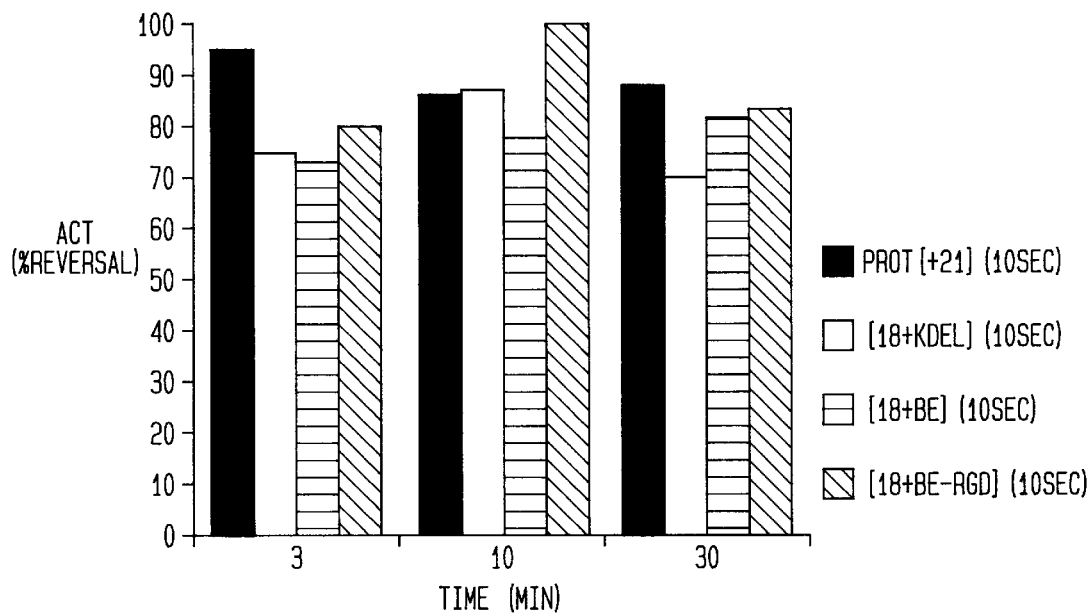
FIG. 5a through FIG. 5d are graphical representations of low molecular weight heparin (Enoxaparin) anticoagulation activities achieved by n-protamine (Protamine [+21]) and the synthetic protamine-like peptide analogs shown in FIG. 4a through FIG. 4d plotted as a percent of reversal against time in minutes, more specifically.
Figure 5B:
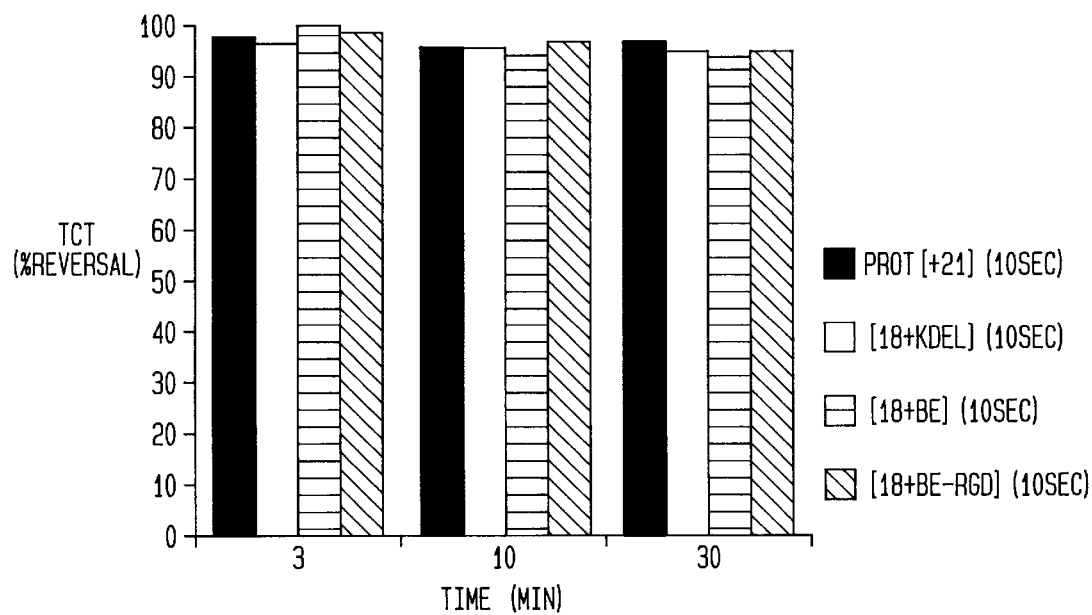
Figure 5C:
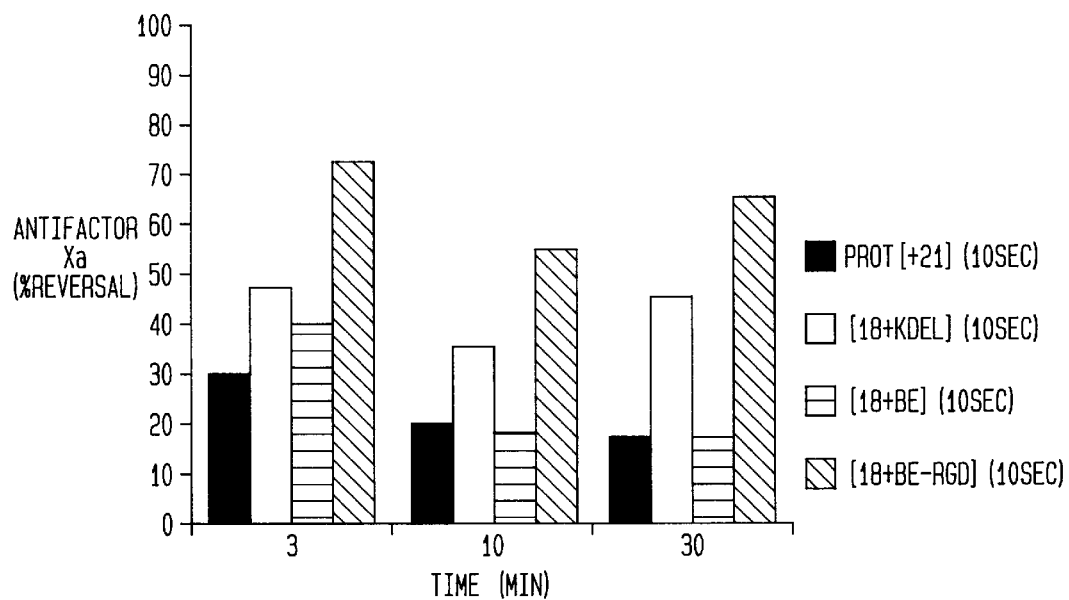
Figure 5D:
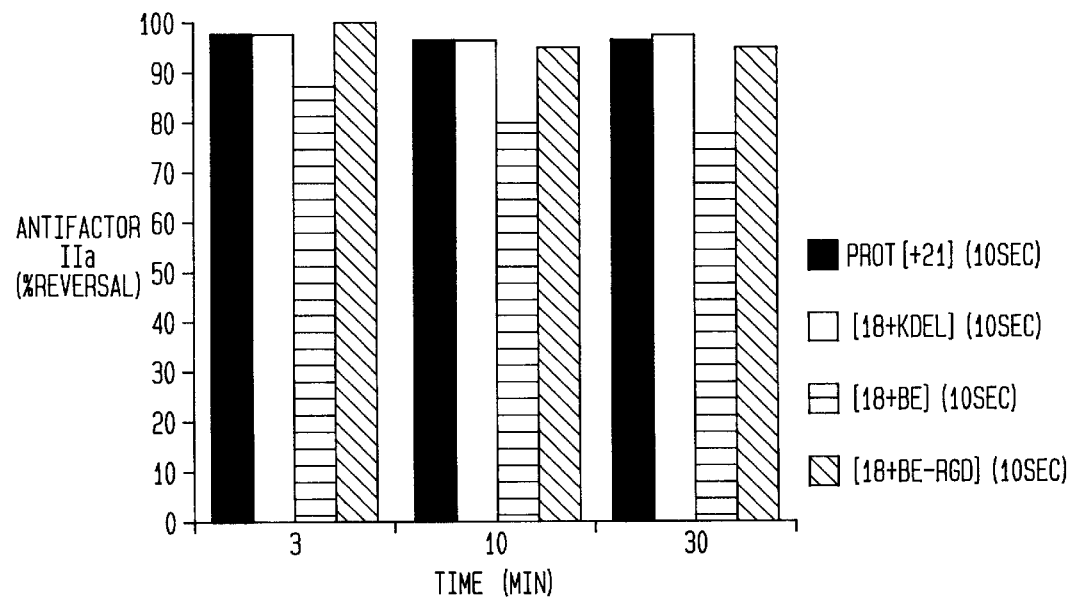

Similar studies were conducted to assess the ability of the protamine-like peptide analogs described in this section to reverse the anticoagulation effects of the LMWH, Enoxaparin. FIG. 5a through FIG. 5d are graphical representations of LMWH anticoagulation activities achieved by n-protamine (Protamine [+21]), and compounds [+18BE], [+18KDEL], and [+18RGD] plotted as a percent of reversal against time in minutes. FIG. 5a shows activated clotting time (ACT), FIG. 5b shows thrombin clotting time (TCT), FIG. 5c shows heparin antifactor Xa activity, and FIG. 5d shows heparin antifactor IIa activity. Referring to FIG. 5c, compound [+18RGD] dramatically outperforms n-protamine in reversing the heparin antifactor Xa activity of Enoxaparin.

The results of the hemodynamic studies obtained for reversal of the anticoagulation activities of LMWH Enoxaparin are set forth in Table 17 hereinbelow.

TABLE 17

Maximum Hemodynamic Changes
5 Minutes after Administration of Enoxaparin

|  | [+18BE] | [+18KDEL] | [+18RGD] | Prot[+21] |
|---|---|---|---|---|
| Mean BP (mm Mercury) | −1 | −6 | −1 | −7 |
| CO | −5% | −14% | −3% | −23% |
| VO$_2$ | −6% | −10% | −7% | −23% |
| HR (beats/min) | −4 | −11 | −3 | −17 |
| Platelet | −35% | −40% | −31% | −40% |
| Xa Reversal (3 min) | 40% | 48% | 72% | 30% |
| IIa Reversal (3 min) | 88% | 98% | 100% | 98% |
| TTS | −3.89 ± 2.37 | −5.00 ± 3.44 | −2.68 ± 0.88 | −5.77 ± 3.46 |

Protamine produces only a 30% reversal of antifactor Xa activity for in vivo anticoagulation with the LMWH Enoxaparin. In general, the smaller the heparin, the greater the inhibition of antifactor Xa activity. Reversal of antifactor Xa activity improved to 40% with [+18BE] and 48% with [+18KDEL]. However, [+18RGD] improved reversal of antifactor Xa to 72%, which is more than double the activity of n-protamine with respect to this LMWH. In addition, [+18RGD] produced less decrease in platelet count than n-protamine.

The TTS for the reversal of Enoxaparin by the protamine-like peptide variants of Table 17 are set forth in Table 18.

TABLE 18

| Charge | Total Toxicity Score |
|---|---|
| [+18BE] | −3.89 ± 2.37 |
| [+18KDEL] | −5.0 ± 3.44 |
| [+18RGD] | −2.68 ± 0.88 |
| [+21] | −5.77 ± 3.46 |
| n-protamine | |

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

---

What is claimed is:

1. A peptide composition comprising at least one peptide having a sequence of about 20–40 uncharged and charged amino acids having a total cationic charge on the order of about [+21], but not less than [+14], as determined by the number of positively charged amino acids in the sequence, at least some of the amino acids in the sequence comprising one or more sequences of RGD cell adhesion ligand, and having the ability to at least partially reverse the effects of heparin and/or low molecular weight heparin anticoagulation with less toxicity in vivo than n-protamine; and a delivery vehicle.

2. The peptide composition of claim 1 wherein the total cationic charge is in the range of [+16] to [+18].

3. The peptide composition of claim 2 wherein the total cationic charge is [+18].

4. The peptide composition of claim 1 wherein the positively charged amino acids are grouped in clusters which are separated by neutral amino acids.

5. The peptide composition of claim 4 wherein the sequence comprises 28–32 amino acids and the positively charged amino acids are grouped in 4 to 5 clusters of 2 to 4 positively charged amino acids which are separated by 2 to 6 neutral amino acids so that the total cationic charge on the peptide is in the range of [+16] to [+18].

6. The peptide composition of claim 4 wherein at least one of the neutral amino acids separating the positively charged clusters is alanine.

7. The peptide composition of claim 1 wherein the positively charged amino acids are distributed evenly along the peptide sequence.

8. The peptide composition of claim 1 wherein the positively charged amino acids are distributed randomly along the peptide sequence.

9. The peptide composition of claim 1 wherein the sequence of amino acids has a C-terminus and an N-terminus at least one of which is modified to be resistant to in vivo degradation.

10. The peptide composition of claim 9 wherein the C-terminus of the sequence is amidated.

11. The peptide composition of claim 10 wherein the N-terminus of the sequence is acetylated.

12. The peptide composition of claim 1 or 9 wherein there is a non-α-helix forming amino acid at the N-terminus of the sequence.

13. The peptide composition of claim 1 or 9 wherein there is an α-helix forming amino acid at the N-terminus of the sequence.

14. The peptide composition of claim 1 wherein the number of amino acids in the sequence is selected to facilitate α-helix formation upon binding with heparin/low molecular weight heparin.

15. The peptide composition of claim 1 wherein the amino acids of the sequence facilitate formation of an α-helix upon binding.

16. A peptide composition comprising at least one peptide having a sequence of about 20–40 uncharged and charged amino acids having a total cationic charge on the order of about [+21], but not less than [+14], as determined by the number of positively charged amino acids in the sequence, at least some of the amino acids in the sequence comprising one or more sequences of YIGSR (Sequence Listing ID No. 18) cell adhesion ligand, and having the ability to at least partially reverse the effects of heparin and/or low molecular weight heparin anticoagulation with less toxicity in vivo than n-protamine; and a delivery vehicle.

17. The peptide composition of claim 16 wherein the total cationic charge is in the range of [+16] to [+18].

18. The peptide composition of claim 17 wherein the total cationic charge is [+18].

19. The peptide composition of claim 16 wherein the positively charged amino acids are grouped in clusters which are separated by neutral amino acids.

20. The peptide composition of claim 19 wherein the sequence comprises 28–32 amino acids and the positively charged amino acids are grouped in 4 to 5 clusters of 2 to 4 positively charged amino acids which are separated by 2 to 6 neutral amino acids so that the total cationic charge on the peptide is in the range of [+16] to [+18].

21. The peptide composition of claim 19 wherein at least one of the neutral amino acids separating the positively charged clusters is alanine.

22. The peptide composition of claim 16 wherein the positively charged amino acids are distributed evenly along the peptide sequence.

23. The peptide composition of claim 16 wherein the positively charged amino acids are distributed randomly along the peptide sequence.

24. The peptide composition of claim 16 wherein the sequence of amino acids has a C-terminus and an N-terminus at least one of which is modified to be resistant to in vivo degradation.

25. The peptide composition of claim 24 wherein the C-terminus of the sequence is amidated.

26. The peptide composition of claim 25 wherein the N-terminus of the sequence is acetylated.

27. The peptide composition of claim 16 or 24 wherein there is a non-α-helix forming amino acid at the N-terminus of the sequence.

28. The peptide composition of claim 16 or 24 wherein there is an α-helix forming amino acid at the N-terminus of the sequence.

29. The peptide composition of claim 16 wherein the number of amino acids in the sequence is selected to facilitate α-helix formation.

30. The peptide composition of claim 16 wherein the amino acids of the sequence facilitate formation of an α-helix.

37

31. A method of making a less toxic agent for reversing the anticoagulation effects of heparin and/or low molecular weight heparin comprising the step of:

preparing a peptide comprising a sequence of 20–40 uncharged and charged amino acids having a total cationic charge in the range of [+16] to [+18], as determined by the number of positively charged amino acids in the sequence, at least some of the amino acids in the sequence comprising one or more sequences of a cell adhesion ligand selected from the group consisting of RGD and YIGSR (Sequence Listing ID No. 18), the peptide having the ability to at least partially reverse the effects of heparin or low molecular weight heparin anticoagulation.

32. The method of claim 31 further including the step of modifying the C-terminus and/or N-terminus of the sequence of amino acids to render the peptide resistant to in vivo degradation.

33. The method of claim 32 wherein the step of modifying the C-terminus of the sequence of amino acids comprises the step of amidating.

34. The method of claim 32 wherein the step of modifying the N-terminus of the sequence of amino acids comprises the step of acetylating.

35. A protamine-like peptide analog having the molecular formula acetyl-EA($R_2A_2R_2A$)$_4R_2$GRGDSPA-amide (Sequence Listing ID No. 5).

36. A polycationic peptide which is an analog of n-protamine wherein the positive charge on the amino acid sequence of n-protamine is reduced by replacement of selected ones of the positively charged arginine residues in naturally-occurring n-protamine with an uncharged amino acid residue so that the total cationic charge on the peptide is less than [+21], but not lower than [+14] and at least some of the amino acids in the sequence comprising one or more sequences of a cell adhesion ligand selected from the group consisting of RGD and YIGSR (Sequence Listing ID No. 18).

37. The polycationic peptide of claim 36 wherein the total cationic charge is in the range of [+16] to [+18].

38. The polycationic peptide of claim 36 wherein selected ones of the arginine residues of naturally-occurring n-protamine are replaced with another positively charged amino acid residue.

39. The polycationic peptide of claim 38 wherein the another positively charged amino acid residue is selected from the group consisting of lysine and histidine.

40. The polycationic peptide of claim 39 wherein the another positively charged amino acid residue is lysine.

41. The polycationic peptide of claim 36 wherein the uncharged amino acid residues are selected from the group consisting of glycine, glutamine, alanine, serine, threonine, asparagine, proline, valine, isoleucine, and leucine.

42. The polycationic peptide of claim 41 wherein the uncharged amino acid residues are glutamine.

43. The polycationic peptide of claim 41 wherein the uncharged amino acid residues are glycine.

44. The polycationic peptide of claim 36 wherein the polycationic peptide sequence of amino acids has a C-terminus and an N-terminus at least one of which is modified to be resistant to in vivo degradation.

45. The polycationic peptide of claim 36 or 44 wherein at least one non-α-helix forming amino acid in the amino acid sequence of n-protamine is replaced with an α-helix forming amino acid.

46. A polycationic peptide which is an analog of n-protamine wherein the positive charge on the amino acid sequence of n-protamine is reduced by replacement of selected ones of the positively charged arginine residues in naturally-occurring n-protamine with glutamine so that the total cationic charge on the peptide is less than [+21], but not lower than [+14] and at least some of the amino acids in the sequence comprising one or more sequences of a cell adhesion ligand selected from the group consisting of RGD and YIGSR (Sequence Listing ID No. 18).

47. A polycationic peptide which is an analog of n-protamine wherein the positive charge on the amino acid sequence of n-protamine is reduced by replacement of selected ones of the positively charged arginine residues in naturally-occurring n-protamine with glycine so that the total cationic charge on the peptide is less than [+21], but not lower than [+14] and at least some of the amino acids in the sequence comprising one or more sequences of a cell adhesion ligand selected from the group consisting of RGD and YIGSR (Sequence Listing ID No. 18).

48. The method of claim 31 or 32 wherein the peptide further has a non-α-helix forming amino acid at the N-terminus of the sequence.

49. The method of claim 31 or 32 wherein the peptide has a α-helix forming amino acid at the N-terminus of the sequence.

50. The method of claim 31 further including the step of mixing the peptide with a delivery vehicle.

51. A method of reversing the anticoagulation effects of heparin and/or low molecular weight heparin comprising administering to a living being an anticoagulation-reversing effective amount of at least one peptide having a sequence of about 20–40 uncharged and charged amino acids having a total cationic charge on the order of about [+21], but not less than [+14], as determined by the number of positively charged amino acids in the sequence, and at least some of the amino acids in the sequence comprising one or more sequences of a cell adhesion ligand selected from the group consisting of RGD and YIGSR (Sequence Listing ID NO. 18), and having the ability to at least partially reverse the effects of heparin and/or low molecular weight heparin anticoagulation with less toxicity in vivo than n-protamine; and a delivery vehicle.

52. A peptide comprising at least one peptide having a sequence of about 20–40 uncharged and charged amino acids having a total cationic charge on the order of about [+21], but not less than [+14], as determined by the number of positively charged amino acids in the sequence, at least some of the amino acids in the sequence comprising one or more sequences of RGD cell adhesion ligand, and having the ability to at least partially reverse the effects of heparin and/or low molecular weight heparin anticoagulation with less toxicity in vivo than n-protamine.

53. The peptide of claim 52 wherein the total cationic charge is in the range of [+16] to [+18].

54. The peptide of claim 53 wherein the total cationic charge is [+18].

55. The peptide of claim 52 wherein the positively charged amino acids are grouped in clusters which are separated by neutral amino acids.

56. The peptide of claim 55 wherein the sequence comprises 28–32 amino acids and the positively charged amino acids are grouped in 4 to 5 clusters of 2 to 4 positively charged amino acids which are separated by 2 to 6 neutral amino acids so that the total cationic charge on the peptide is in the range of [+16] to [+18].

57. The peptide of claim 53 wherein at least one of the neutral amino acids separating the positively charged clusters is alanine.

58. The peptide of claim 52 wherein the positively charged amino acids are distributed evenly along the peptide sequence.

59. The peptide of claim 52 wherein the positively charged amino acids are distributed randomly along the peptide sequence.

60. The peptide of claim 52 wherein the sequence of amino acids has a C-terminus and an N-terminus at least one of which is modified to be resistant to in vivo degradation.

61. The peptide of claim 60 wherein the C-terminus of the sequence is amidated.

62. The peptide of claim 61 wherein the N-terminus of the sequence is acetylated.

63. The peptide of claim 52 or 60 wherein there is a non-α-helix forming amino acid at the N-terminus of the sequence.

64. The peptide of claim 52 or 60 wherein there is an α-helix forming amino acid at the N-terminus 109 of the sequence.

65. The peptide of claim 52 wherein the number of amino acids in the sequence is selected to facilitate α-helix formation.

66. The peptide of claim 52 wherein the amino acids of the sequence facilitate formation of an α-helix.

67. A peptide comprising a sequence of 20–40 uncharged and charged amino acids having a total cationic charge of less than [+21], but not lower than [+14], as determined by the number of positively charged amino acids in the sequence, at least some of the amino acids in the sequence comprising one or more sequences of YIGSR (Sequence Listing ID No. 18) cell adhesion ligand, and having the ability to at least partially reverse the effects of heparin and/or low molecular weight heparin anticoagulation with less toxicity in vivo than n-protamine.

68. The peptide of claim 67 wherein the total cationic charge is in the range of [+16] to [+18].

69. The peptide of claim 68 wherein the total cationic charge is [+18].

70. The peptide of claim 67 wherein the positively charged amino acids are grouped in clusters which are separated by neutral amino acids.

71. The peptide of claim 67 wherein the sequence comprises 28–32 amino acids and the positively charged amino acids are grouped in 4 to 5 clusters of 2 to 4 positively charged amino acids which are separated by 2 to 6 neutral amino acids so that the total cationic charge on the peptide is in the range of [+16] to [+18].

72. The peptide of claim 67 wherein at least one of the neutral amino acids separating the positively charged clusters is alanine.

73. The peptide of claim 67 wherein the positively charged amino acids are distributed evenly along the peptide sequence.

74. The peptide of claim 67 wherein the positively charged amino acids are distributed randomly along the peptide sequence.

75. The peptide of claim 67 wherein the sequence of amino acids has a C-terminus and an N-terminus at least one of which is modified to be resistant to in vivo degradation.

76. The peptide of claim 65 wherein the C-terminus of the sequence is amidated.

77. The peptide of claim 35 wherein the N-terminus of the sequence is acetylated.

78. The peptide of claim 67 or 65 wherein there is a non-α-helix forming amino acid at the N-terminus of the sequence.

79. The peptide of claim 67 or 65 wherein there is an α-helix forming amino acid at the N-terminus of the sequence.

80. The peptide of claim 67 wherein the number of amino acids in the sequence is selected to facilitate α-helix formation.

81. The peptide of claim 67 wherein the amino acids of the sequence facilitate formation of an α-helix.

* * * * *

UNITED STATES PATENT AND TRADEMARK OFFICE
CERTIFICATE OF CORRECTION

PATENT NO. : 5,919,761
DATED : July 6, 1999
INVENTOR(S) : Thomas W. Wakefield, James C. Stanley and Philip C. Andrews It is certified that error appears in the above-indentified patent and that said Letters Patent is hereby corrected as shown below:

Col 6, lines 45-55, Table 1, at Amino Acid Sequence (1), change "YP(KA)$_{13}$K" to -- TP(KA)$_{13}$K --;

Col. 6, lines 45-55, Table 1, at Amino Acid Sequence (8), change "PK$_4$S$_3$KPVK$_6$PKVSK$_6$G$_2$K$_4$" to -- PK$_4$S$_3$KPVK$_5$PKVSK$_6$G$_2$K$_4$ --;

Col. 12, lines 10-28, Table 6, in the "Charge" column, change "[+186]" to -- [+18B] --;

Col. 15, line 29, after "-43% for" -- insert protamine --;

Claim 57, lines 1, change "53" to -- 55 --;

Claim 64, line 2, delete "109";

Claim 71, line 1, change "67" to -- 70 --;

Claim 72, line 1, change "67" to -- 70 --;

Claim 76, line 1, "65" should read --67--;

UNITED STATES PATENT AND TRADEMARK OFFICE
CERTIFICATE OF CORRECTION

PATENT NO. : 5,919,761
DATED : July 6, 1999
INVENTOR(S) : Thomas W. Wakefield, James C. Stanley and Philip C. Andrews It is certified that error appears in the above-identified patent and that said Letters Patent is hereby corrected as shown below:

Claim 77, line 1, change "35" to -- 76 --;

Claim 78, line 1, change "65" to -- 75 --; and

Claim 79, line 1, change "65" to -- 75 --.

Signed and Sealed this

Fifth Day of December, 2000

Attest:

Attesting Officer

Q. TODD DICKINSON

Director of Patents and Trademarks

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 28 amino acids
      (B) TYPE: amino acid
      (C) STRANDEDNESS: Not Relevant
      (D) TOPOLOGY: Not Relevant (ii) MOLECULE TYPE: peptide (vi) ORIGINAL SOURCE:
      (A) ORGANISM: N/A (x) PUBLICATION INFORMATION:
      (A) AUTHORS: N/A
      (B) TITLE: N/A (xi) SEQUENCE DESCRIPTION: SEQ ID NO:1:

Pro Ala Lys Lys Ala Lys Lys Ala Ala Lys
                5                       10

Lys Ala Lys Lys Ala Ala Lys Lys Ala Lys
                15                     20

Lys Ala Ala Lys Lys Ala Lys Lys
                25

(2) INFORMATION FOR SEQ ID NO:2:

(i) SEQUENCE CHARACTERISTICS:
      (A) LENGTH: 32 amino acids
      (B) TYPE: amino acid (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:2:

Pro Ala Lys Lys Ala Ala Lys Lys Ala Lys
                5                  10

Lys Ala Ala Lys Lys Ala Lys Lys Ala Ala
               15                  20

Lys Lys Ala Lys Lys Ala Ala Lys Lys Ala
               25                  30

Lys Lys (2) INFORMATION FOR SEQ ID NO:3:

(i) SEQUENCE CHARACTERISTICS:
        (A) LENGTH:                29 amino acids
        (B) TYPE:                  amino acid
        (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:3:

Glu Ala Lys Lys Ala Ala Lys Lys Ala Lys
                5                  10

Lys Ala Ala Lys Lys Ala Lys Lys Ala Ala
               15                  20

Lys Lys Ala Lys Lys Ala Ala Lys Lys
               25

(2) INFORMATION FOR SEQ ID NO:4:

(i) SEQUENCE CHARACTERISTICS:
        (A) LENGTH:                33 amino acids
        (B) TYPE:                  amino acid
        (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:4:

Glu Ala Ala Lys Lys Ala Ala Lys Lys Ala
                5                  10

Lys Lys Ala Ala Lys Lys Ala Lys Lys Ala
               15                  20

```
Ala Lys Lys Ala Lys Lys Ala Ala Lys Lys
                25                  30

Ala Lys Lys
```

(2) INFORMATION FOR SEQ ID NO:5:

(i) SEQUENCE CHARACTERISTICS:
        (A) LENGTH:                39 amino acids
        (B) TYPE:                    amino acid
        (C) STRANDEDNESS: Not Relevant
        (D) TOPOLOGY: Not Relevant (ii) MOLECULE TYPE:        peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:5:

```
Glu Ala Arg Arg Ala Ala Arg Arg Ala Arg
                 5                  10

Arg Ala Ala Arg Arg Ala Arg Arg Ala Ala
                15                  20

Arg Arg Ala Arg Arg Ala Ala Arg Arg Ala
                25                  30

Arg Arg Gly Arg Gly Asp Ser Pro Ala
                35
```

(2) INFORMATION FOR SEQ ID NO:6:

(i) SEQUENCE CHARACTERISTICS:
        (A) LENGTH:                29 amino acids
        (B) TYPE:                    amino acid
        (C) STRANDEDNESS: Not Relevant
        (D) TOPOLOGY: Not Relevant (ii) MOLECULE TYPE:        peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:6:

```
Pro Lys Lys Gln Gln Gly Gly Gly Gly Lys
                 5                  10

Lys Gln Gln Gly Gly Gly Gly Lys Lys Gln
                15                  20

Gln Gly Gly Gly Gly Lys Lys Gln Gln
                25
```

(2) INFORMATION FOR SEQ ID NO:7:

(i) SEQUENCE CHARACTERISTICS:
        (A) LENGTH:                28 amino acids
        (B) TYPE:                    amino acid
        (C) STRANDEDNESS: Not Relevant
        (D) TOPOLOGY: Not Relevant (ii) MOLECULE TYPE:        peptide (vi) ORIGINAL SOURCE:
        (A) ORGANISM:            N/A (x) PUBLICATION INFORMATION:
    (A) AUTHORS:         N/A
    (B) TITLE:           N/A (xi) SEQUENCE DESCRIPTION: SEQ ID NO:7:

Pro Lys Gly Lys Gly Lys Gly Lys Gly Lys
                 5                  10
Gly Lys Gly Lys Gly Lys Gly Lys Gly Lys
                15                  20
Gly Lys Gly Lys Gly Lys Gly Lys
                25

(2) INFORMATION FOR SEQ ID NO:8:

(i) SEQUENCE CHARACTERISTICS:
        (A) LENGTH:              29 amino acids
        (B) TYPE:                amino acid
        (C) STRANDEDNESS: Not Relevant
        (D) TOPOLOGY: Not Relevant (ii) MOLECULE TYPE:          peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:8:

Thr Pro Lys Ala Lys Ala Lys Ala Lys Ala
                 5                  10
Lys Ala Lys Ala Lys Ala Lys Ala Lys Ala
                15                  20
Lys Ala Lys Ala Lys Ala Lys Ala Lys
                25

(2) INFORMATION FOR SEQ ID NO:9:

(i) SEQUENCE CHARACTERISTICS:
        (A) LENGTH:              29 amino acids
        (B) TYPE:                amino acid
        (C) STRANDEDNESS: Not Relevant
        (D) TOPOLOGY: Not Relevant (ii) MOLECULE TYPE:          peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:9:

Pro Lys Lys Lys Lys Gly Gly Gly Gly Lys
                 5                  10
Lys Lys Lys Gly Gly Gly Gly Lys Lys Lys
                15                  20
Lys Gly Gly Gly Gly Lys Lys Lys Lys
                25

(2) INFORMATION FOR SEQ ID NO:10:

(i) SEQUENCE CHARACTERISTICS:
        (A) LENGTH:              29 amino acids
        (B) TYPE:                amino acid
        (C) STRANDEDNESS: Not Relevant (D) TOPOLOGY: Not Relevant (ii) MOLECULE TYPE:             peptide (vi) ORIGINAL SOURCE:
            (A) ORGANISM:            N/A (x) PUBLICATION INFORMATION:
            (A) AUTHORS:             N/A
            (B) TITLE:               N/A (xi) SEQUENCE DESCRIPTION: SEQ ID NO:10:

Pro Lys Lys Lys Lys Gly Gly Gly Gly Lys
                5                   10

Lys Lys Lys Gly Gly Lys Lys Lys Lys Gly
            15                  20

Gly Lys Lys Lys Gly Gly Lys Lys
            25

(2) INFORMATION FOR SEQ ID NO:11:

(i) SEQUENCE CHARACTERISTICS:
            (A) LENGTH:              30 amino acids
            (B) TYPE:                amino acid
            (C) STRANDEDNESS: Not Relevant
            (D) TOPOLOGY: Not Relevant (ii) MOLECULE TYPE:             peptide (vi) ORIGINAL SOURCE:
            (A) ORGANISM:            N/A (x) PUBLICATION INFORMATION:
            (A) AUTHORS:             N/A
            (B) TITLE:               N/A (xi) SEQUENCE DESCRIPTION: SEQ ID NO:11:

Pro Lys Lys Gly Lys Lys Gly Lys Lys Gly
                5                   10

Lys Lys Gly Lys Lys Gly Lys Lys Gly Lys
            15                  20

Lys Gly Lys Lys Gly Lys Lys Gly Lys Lys
            25                  30

(2) INFORMATION FOR SEQ ID NO:12:

(i) SEQUENCE CHARACTERISTICS:
            (A) LENGTH:              29 amino acids
            (B) TYPE:                amino acid
            (C) STRANDEDNESS: Not Relevant
            (D) TOPOLOGY: Not Relevant (ii) MOLECULE TYPE:             peptide (vi) ORIGINAL SOURCE:
            (A) ORGANISM:            N/A (x) PUBLICATION INFORMATION:
            (A) AUTHORS:             N/A
            (B) TITLE:               N/A (xi) SEQUENCE DESCRIPTION: SEQ ID NO:12:

Pro Lys Lys Lys Lys Gly Gly Lys Lys Lys
                5                   10

Lys Gly Gly Lys Lys Lys Lys Gly Gly Lys
            15                  20

Lys Lys Lys Gly Gly Lys Lys Lys Lys
            25

(2) INFORMATION FOR SEQ ID NO:13:

(i) SEQUENCE CHARACTERISTICS:
        (A) LENGTH:                32 amino acids
        (B) TYPE:                  amino acid
        (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:13:

Pro Lys Lys Lys Lys Ser Ser Ser Lys Pro
                5                   10

Val Lys Lys Lys Lys Lys Pro Lys Val Ser
                15                  20

Lys Lys Lys Lys Lys Lys Gly Gly Lys Lys
                25                  30

Lys Lys (2) INFORMATION FOR SEQ ID NO:14:

(i) SEQUENCE CHARACTERISTICS:
        (A) LENGTH:                32 amino acids
        (B) TYPE:                  amino acid
        (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:14:

Pro Arg Arg Arg Arg Ser Ser Ser Arg Pro
                5                   10

Val Arg Arg Arg Arg Arg Pro Arg Val Ser
                15                  20

Arg Arg Arg Arg Arg Arg Gly Gly Arg Arg
                25                  30

Arg Arg (2) INFORMATION FOR SEQ ID NO:15:

(i) SEQUENCE CHARACTERISTICS:
        (A) LENGTH:                29 amino acids
        (B) TYPE:                  amino acid
        (C) STRANDEDNESS: Not Relevant
        (D) TOPOLOGY: Not Relevant (ii) MOLECULE TYPE:            peptide (vi) ORIGINAL SOURCE:
        (A) ORGANISM:              N/A (x) PUBLICATION INFORMATION:
        (A) AUTHORS:               N/A
        (B) TITLE:                 N/A (xi) SEQUENCE DESCRIPTION: SEQ ID NO:15:

Pro Ala Lys Lys Ala Ala Lys Lys Ala Lys
                 5                  10

Lys Ala Ala Lys Lys Ala Lys Lys Ala Ala
                15                  20

Lys Lys Ala Lys Lys Ala Ala Lys Lys
                25

(2) INFORMATION FOR SEQ ID NO:16:

(i) SEQUENCE CHARACTERISTICS:
        (A) LENGTH:              29 amino acids
        (B) TYPE:                amino acid
        (C) STRANDEDNESS: Not Relevant
        (D) TOPOLOGY: Not Relevant (ii) MOLECULE TYPE:          peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:16:

Pro Lys Lys Lys Ala Ala Lys Lys Ala Lys
                 5                  10

Lys Ala Ala Lys Lys Ala Lys Lys Ala Ala
                15                  20

Lys Lys Ala Lys Lys Ala Lys Lys Lys
                25

(2) INFORMATION FOR SEQ ID NO:17:

(i) SEQUENCE CHARACTERISTICS:
        (A) LENGTH:              38 amino acids
        (B) TYPE:                amino acid
        (C) STRANDEDNESS: Not Relevant
        (D) TOPOLOGY: Not Relevant (ii) MOLECULE TYPE:          peptide (vi) ORIGINAL SOURCE:
        (A) ORGANISM:            N/A (x) PUBLICATION INFORMATION:
        (A) AUTHORS:             N/A
        (B) TITLE:               N/A (xi) SEQUENCE DESCRIPTION: SEQ ID NO:17:

Glu Ala Arg Arg Ala Ala Arg Arg Ala Arg
                 5                  10

Arg Ala Ala Arg Arg Ala Arg Arg Ala Ala
                15                  20

Arg Arg Ala Arg Arg Ala Ala Arg Arg Ala
                25                  30

Arg Arg Gly Val Lys Asp Glu Leu
                35

(2) INFORMATION FOR SEQ ID NO:18:

(i) SEQUENCE CHARACTERISTICS:
        (A) LENGTH:              5 amino acids
        (B) TYPE:                amino acid
        (C) STRANDEDNESS: Not Relevant
        (D) TOPOLOGY: Not Relevant

```
        (ii) MOLECULE TYPE:              peptide (vi) ORIGINAL SOURCE:
             (A) ORGANISM:               N/A (x) PUBLICATION INFORMATION:
             (A) AUTHORS:                N/A
             (B) TITLE:                  N/A (xi) SEQUENCE DESCRIPTION: SEQ ID NO:18:

Tyr Ile Gly Ser Arg
```